(12) United States Patent
Chen et al.

(10) Patent No.: US 10,894,980 B2
(45) Date of Patent: Jan. 19, 2021

(54) METHODS OF AMPLIFYING NUCLEIC ACID SEQUENCES MEDIATED BY TRANSPOSASE/TRANSPOSON DNA COMPLEXES

(71) Applicant: President and Fellows of Harvard College, Cambridge, MA (US)

(72) Inventors: Chongyi Chen, Somerville, MA (US); Dong Xing, Cambridge, MA (US); Xiaoliang Sunney Xie, Lexington, MA (US)

(73) Assignee: President and Fellows of Harvard College, Cambridge, MA (US)

(*) Notice: Subject to any disclaimer, the term of this patent is extended or adjusted under 35 U.S.C. 154(b) by 62 days.

(21) Appl. No.: 15/745,251

(22) PCT Filed: Jul. 15, 2016

(86) PCT No.: PCT/US2016/042394
§ 371 (c)(1),
(2) Date: Jan. 16, 2018

(87) PCT Pub. No.: WO2017/015075
PCT Pub. Date: Jan. 26, 2017

(65) Prior Publication Data
US 2019/0002967 A1    Jan. 3, 2019

Related U.S. Application Data

(60) Provisional application No. 62/193,733, filed on Jul. 17, 2015.

(51) Int. Cl.
*C12P 19/34*    (2006.01)
*C12Q 1/6865*    (2018.01)

(52) U.S. Cl.
CPC .................. *C12Q 1/6865* (2013.01)

(58) Field of Classification Search
None
See application file for complete search history.

(56) References Cited

U.S. PATENT DOCUMENTS

| 2006/0014169 | A1 | 1/2006 | Fiandt et al. |
| 2007/0031857 | A1* | 2/2007 | Makarov ............ C12P 19/34 435/6.18 |

(Continued)

FOREIGN PATENT DOCUMENTS

| WO | 2012/061832 A1 | 5/2012 |
| WO | 2014/143158 A1 | 9/2014 |
| WO | 2016/138292 A1 | 9/2016 |

OTHER PUBLICATIONS

Picelli, Simone et al., "Tn5 transposase and tagmentation procedures for massively scaled sequencing projects", Genome Research, vol. 24, No. 12, Jul. 30, 2014 (Jul. 30, 2014), pp. 2033-2040.
(Continued)

*Primary Examiner* — Kenneth R Horlick
(74) *Attorney, Agent, or Firm* — Banner & Witcoff, Ltd.

(57) ABSTRACT

Methods are provided for nucleic acid amplification including contacting a double stranded nucleic acid with transposases bound to transposon DNA, wherein the transposon DNA includes a transposase binding site and an RNA polymerase promoter sequence, wherein the transposases/transposon DNA complex bind to target locations along the double stranded nucleic acid and cleave the double stranded nucleic acid into a plurality of double stranded fragments, with each double stranded fragment having the transposon DNA bound to each 5' end of the double stranded fragment, extending the double stranded fragments along the transposon DNA to make double stranded extension products having double stranded RNA polymerase promoter sequences at each end, contacting the double stranded extension products with an RNA polymerase to make a plurality (Continued)

of RNA transcripts of each double stranded extension product, reverse transcribing the RNA transcripts into single stranded copy DNA, forming complementary strands to the single stranded copy DNA to form a plurality of double stranded DNA amplicons corresponding to each double stranded fragment.

20 Claims, 10 Drawing Sheets

(56) References Cited

U.S. PATENT DOCUMENTS

| | | | |
|---|---|---|---|
| 2011/0319290 A1* | 12/2011 | Raymond | C12Q 1/6869 |
| | | | 506/9 |
| 2012/0208705 A1* | 8/2012 | Steemers | C12N 15/1065 |
| | | | 506/2 |
| 2012/0208724 A1* | 8/2012 | Steemers | C12Q 1/6869 |
| | | | 506/26 |
| 2012/0258892 A1 | 10/2012 | Wang | |
| 2013/0196860 A1 | 8/2013 | Grunenwald et al. | |
| 2014/0200146 A1 | 7/2014 | Xie et al. | |

OTHER PUBLICATIONS

Head, Steven R. et al., "Library construction for next-generation sequencing: Overviews and challenges", Biotechniques Rapid Dispatches, vol. 56, No. 2, Feb. 1, 2014 (Feb. 1, 2014).

\* cited by examiner

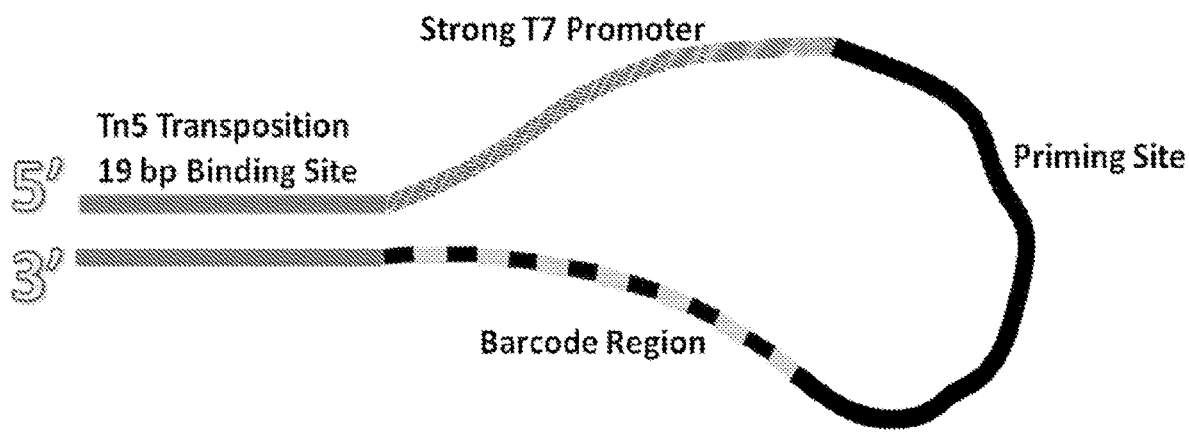
Figure 1
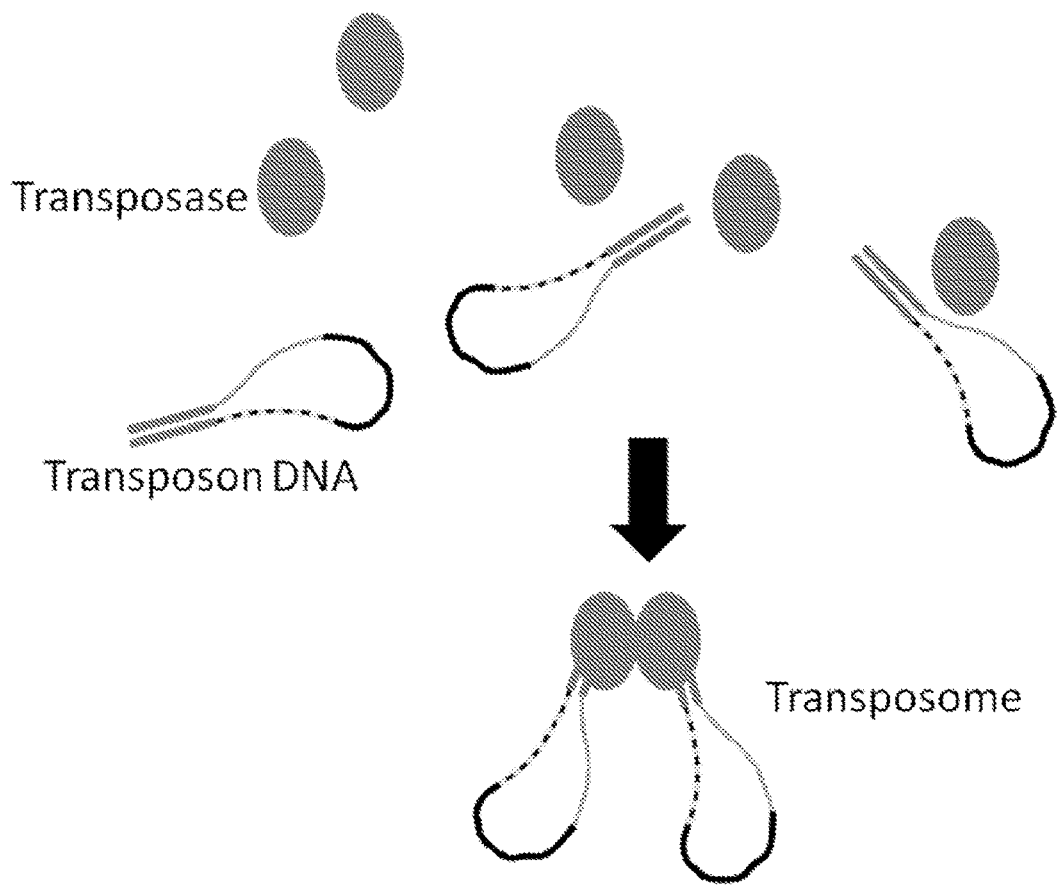
Figure 2a: Transposome formation

Figure 2b: Random transposition

PCR (Exponential Amplification)     IVT (Linear Amplification)
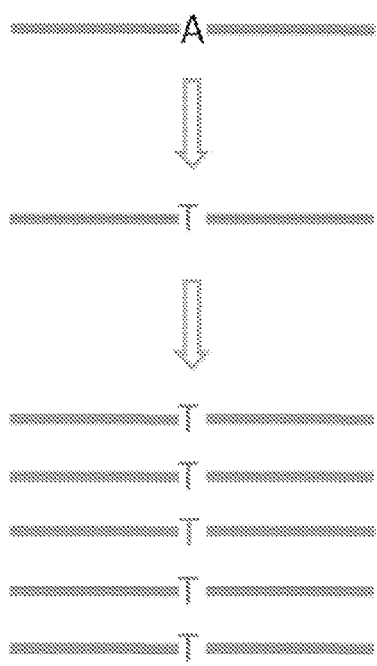
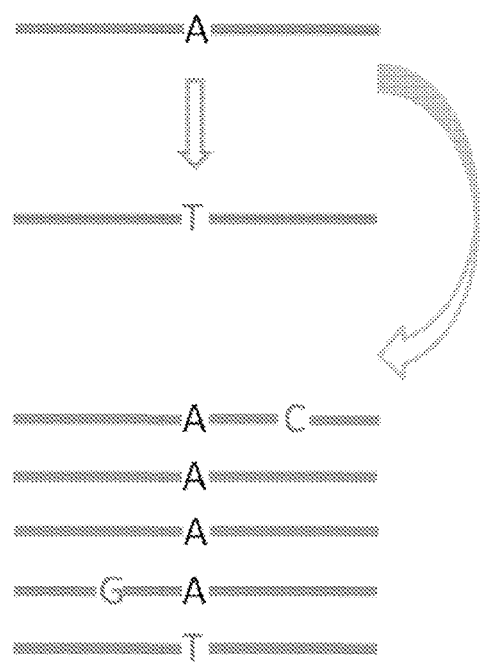
Figure 8
Barcode 1
Barcode 2
Barcode 3
Figure 9

| | |
|---|---|
| Mapped Ratio | 63% |
| Coverage Ratio | 70% |
| Coverage Depth | 14X |
| Allele Drop-out | 55% |
| False Positive | 1E-04 |
| Chimera Rate | 0.77% |

Figure 12

METHODS OF AMPLIFYING NUCLEIC ACID SEQUENCES MEDIATED BY TRANSPOSASE/TRANSPOSON DNA COMPLEXES

RELATED APPLICATIONS

This application is a National Stage Application under 35 U.S.C. 371 of co-pending PCT application PCT/US16/42394 designating the United States and filed Jul. 15, 2016; which claims the benefit of Provisional application No. 62/193,733 and filed Jul. 17, 2015 each of which are hereby incorporated by reference in their entireties.

STATEMENT OF GOVERNMENT INTERESTS

The invention was made with government support under CA186693 awarded by the National Institutes of Health. The government has certain rights in the invention.

BACKGROUND

Field of the Invention

Embodiments of the present invention relate in general to methods and compositions for amplifying trace amount of DNA, such as DNA from a single cell, in order to determine its genetic sequences, particularly the entire genome.

Description of Related Art

The capability to perform single-cell genome sequencing is important in studies where cell-to-cell variation and population heterogeneity play a key role, such as tumor growth, stem cell reprogramming, embryonic development, etc. Single cell genome sequencing is also important when the cell samples subject to sequencing are precious or rare or in minute amounts. Important to accurate single-cell genome sequencing is the initial amplification of the genomic DNA which can be in minute amounts.

Multiple displacement amplification (MDA) is a common method used in the art with genomic DNA from a single cell prior to sequencing and other analysis. In this method, random primer annealing is followed by extension taking advantage of a DNA polymerase with a strong strand displacement activity. The original genomic DNA from a single cell is amplified exponentially in a cascade-like manner to form hyperbranched DNA structures. Another method of amplifying genomic DNA from a single cell is described in Zong, C., Lu, S., Chapman, A. R., and Xie, X. S. (2012), Genome-wide detection of single-nucleotide and copy-number variations of a single human cell, Science 338, 1622-1626 which describes Multiple Annealing and Looping-Based Amplification Cycles (MALBAC). Several other methods used with single cell genomic DNA include Cheung, V. G. and S. F. Nelson, Whole genome amplification using a degenerate oligonucleotide primer allows hundreds of genotypes to be performed on less than one nanogram of genomic DNA, *Proceedings of the National Academy of Sciences of the United States of America*, 1996, 93(25): p. 14676-9; Telenius, H., et al., Degenerate oligonucleotide-primed PCR: general amplification of target DNA by a single degenerate primer, *Genomics*, 1992. 13(3): p. 718-25; Zhang, L., et al., Whole genome amplification from a single cell: implications for genetic analysis. *Proceedings of the National Academy of Sciences of the United States of America*, 1992, 89(13): p. 5847-51; Lao, K., N. L. Xu, and N. A. Straus, Whole genome amplification using single-primer PCR, *Biotechnology Journal*, 2008, 3(3): p. 378-82; Dean, F. B., et al., Comprehensive human genome amplification using multiple displacement amplification, *Proceedings of the National Academy of Sciences of the United States of America*, 2002. 99(8): p. 5261-6; Lage, J. M., et al., Whole genome analysis of genetic alterations in small DNA samples using hyperbranched strand displacement amplification and array-CGH, *Genome Research*, 2003, 13(2): p. 294-307; Spits, C., et al., Optimization and evaluation of single-cell whole-genome multiple displacement amplification, *Human Mutation*, 2006, 27(5): p. 496-503; Cole, J., et al., Massively parallel polymerase cloning and genome sequencing of single cells using nanoliter microwells, *Nature Biotechnology*, 2013. 31(12): p. 1126-32; Jiang, Z., et al., Genome amplification of single sperm using multiple displacement amplification, *Nucleic Acids Research*, 2005, 33(10): p. e91; Wang, J., et al., Genome-wide Single-Cell Analysis of Recombination Activity and De Novo Mutation Rates in Human Sperm, *Cell*, 2012. 150(2): p. 402-12; Hou, Y., et al., Single cell exome sequencing and monoclonal evolution of a JAK2-negative myeloproliferative neoplasm, *Cell*, 2012, 148(5): p. 873-85; Xu, X., et al., Single-cell exome sequencing reveals single-nucleotide mutation characteristics of a kidney tumor, *Cell*, 2012, 148(5): p. 886-95; Evrony, G. D., et al., Single-neuron sequencing analysis of 11 retrotransposition and somatic mutation in the human brain, *Cell*, 2012. 151(3): p. 483-96; and McLean, J. S., et al., Genome of the pathogen Porphyromonas gingivalis recovered from a biofilm in a hospital sink using a high-throughput single-cell genomics platform, *Genome Research*, 2013. 23(5): p. 867-77. Methods directed to aspects of whole genome amplification are reported in WO 2012/166425, U.S. Pat. No. 7,718,403, US 2003/0108870 and U.S. Pat. No. 7,402,386.

However, a need exists for further methods of amplifying small amounts of genomic DNA, such as from a single cell or small group of cells.

SUMMARY

Embodiments of the present disclosure are directed to a method of amplifying DNA such as a small amount of genomic DNA or a limited amount of DNA such as a genomic sequence or genomic sequences obtained from a single cell or a plurality of cells of the same cell type or from a tissue, fluid or blood sample obtained from an individual or a substrate. According to certain aspects of the present disclosure, the methods described herein can be performed in a single tube with a single reaction mixture. According to certain aspects of the present disclosure, the nucleic acid sample can be within an unpurified or unprocessed lysate from a single cell. Nucleic acids to be subjected to the methods disclosed herein need not be purified, such as by column purification, prior to being contacted with the various reagents and under the various conditions as described herein. The methods described herein can provide substantial and uniform coverage of the entire genome of a single cell producing amplified DNA for high-throughput sequencing.

Embodiments of the present invention relate in general to methods and compositions for making DNA fragments, for example, DNA fragments from the whole genome of a single cell which may then be subjected to amplification methods known to those of skill in the art. According to one aspect, a transposase as part of a transposome is used to create a set of double stranded genomic DNA fragments. Each of the double stranded genomic DNA fragments may then be amplified using methods known to those of skill in the art, such as PCR amplification, and as described herein.

According to one particular embodiment, each double stranded DNA (dsDNA) fragment is then used as a template for making multiple copies of a corresponding RNA. According to this aspect, the original dsDNA template is used to make each of the multiple copies of the corresponding RNA. The multiple copies of the RNA corresponding to the original dsDNA fragment template are then reverse transcribed to create multiple copies of single stranded DNA corresponding to the original dsDNA fragment template. Complementary strands are then made for the multiple copies of the ssDNA creating multiple copies of dsDNA corresponding to the original dsDNA fragment template. In this manner, the original dsDNA template fragment has been linearly amplified. That is, the dsDNA template fragment is the original source template for the dsDNA amplicons corresponding to the dsDNA template fragment. Amplicons of the dsDNA template fragment are not themselves amplified to create amplicons from amplicons. The dsDNA amplicons of the present disclosure are linearly amplified from an original dsDNA fragment template.

According to certain aspects, methods of making nucleic acid fragments described herein utilize a transposase. The transposase is complexed with a transposon DNA including a double stranded transposase binding site and a first nucleic acid sequence including one or more of a barcode sequence and a priming site to form a transposase/transposon DNA complex. The first nucleic acid sequence may be in the form of a single stranded extension or the first nucleic acid sequence may be in the form of a loop with each end connected to a corresponding strand of the double stranded transposase binding site. According to certain aspects, the transposases have the capability to bind to the transposon DNA and dimerize when contacted together, such as when being placed within a reaction vessel, forming a transposase/transposon DNA complex dimer called transposome. The transposome have the capability to bind to target locations along double stranded nucleic acids, such as double stranded genomic DNA, forming a complex including the transposome and the double stranded genomic DNA. The transposases in the transposome cleave the double stranded genomic DNA, with one transposase cleaving the upper strand and one transposase cleaving the lower strand. The transposon DNA in the transposome is attached to the double stranded genomic DNA at the cut site. According to certain aspects, a plurality of transposase/transposon DNA complex dimers bind to a corresponding plurality of target locations along a double stranded genomic DNA, for example, and then cleave the double stranded genomic DNA into a plurality of double stranded fragments with each fragment having transposon DNA attached at each end of the double stranded fragment. According to one aspect, the transposon DNA is attached to the double stranded genomic DNA and a single stranded gap exists between one strand of the genomic DNA and one strand of the transposon DNA. According to one aspect, gap extension is carried out to fill the gap and create a double stranded connection between the double stranded genomic DNA and the double stranded transposon DNA. According to one aspect, the transposase binding site of the transposon DNA is attached at each end of the double stranded fragment. According to certain aspects, the transposase is attached to the transposon DNA which is attached at each end of the double stranded fragment. According to one aspect, the transposases are removed from the transposon DNA which is attached at each end of the double stranded genomic DNA fragments.

According to one aspect of the present disclosure, the double stranded genomic DNA fragments produced by the transposases which have the transposon DNA attached at each end of the double stranded genomic DNA fragments are then gap filled and extended using the transposon DNA as a template. Accordingly, a double stranded nucleic acid extension product is produced which includes the double stranded genomic DNA and a double stranded transposon DNA at each end of the double stranded genomic DNA. The double stranded nucleic acid extension products may then be amplified using methods known to those of skill in the art, such as PCR.

According to additional certain aspects, methods of making nucleic acid fragments described herein utilize a transposase and an RNA polymerase. The transposase is complexed with a transposon DNA including a double stranded transposase binding site and a first nucleic acid sequence including one or more of a barcode sequence, a priming site and an RNA polymerase promoter sequence to form a transposase/transposon DNA complex. The first nucleic acid sequence may be in the form of a single stranded extension or the first nucleic acid sequence may be in the form of a loop with each end connected to a corresponding strand of the double stranded transposase binding site. According to certain aspects, the transposases have the capability to bind to the transposon DNA and dimerize when contacted together, such as when being placed within a reaction vessel, forming a transposase/transposon DNA complex dimer called transposome. The transposome have the capability to bind to target locations along double stranded nucleic acids, such as double stranded genomic DNA, forming a complex including the transposome and the double stranded genomic DNA. The transposases in the transposome cleave the double stranded genomic DNA, with one transposase cleaving the upper strand and one transposase cleaving the lower strand. The transposon DNA in the transposome is attached to the double stranded genomic DNA at the cut site. According to certain aspects, a plurality of transposase/transposon DNA complexe dimers bind to a corresponding plurality of target locations along a double stranded genomic DNA, for example, and then cleave the double stranded genomic DNA into a plurality of double stranded fragments with each fragment having transposon DNA attached at each end of the double stranded fragment. According to one aspect, the transposon DNA is attached to the double stranded genomic DNA and a single stranded gap exists between one strand of the genomic DNA and one strand of the transposon DNA. According to one aspect, gap extension is carried out to fill the gap and create a double stranded connection between the double stranded genomic DNA and the double stranded transposon DNA. According to one aspect, the transposase binding site of the transposon DNA is attached at each end of the double stranded fragment. According to certain aspects, the transposase is attached to the transposon DNA which is attached at each end of the double stranded fragment. According to one aspect, the transposases are removed from the transposon DNA which is attached at each end of the double stranded genomic DNA fragments.

According to one aspect of the present disclosure, the double stranded genomic DNA fragments produced by the transposases which have the transposon DNA attached at each end of the double stranded genomic DNA fragments are then gap filled and extended using the transposon DNA as a template. Accordingly, a double stranded nucleic acid extension product is produced which includes the double stranded genomic DNA and a double stranded transposon DNA at each end of the double stranded genomic DNA. Since the double stranded transposon DNA may include an active double stranded RNA polymerase promoter sequence, an RNA polymerase can then be used to make many RNA transcripts of the double stranded nucleic acid extension product using the double stranded nucleic acid extension product as a template for each of the many or plurality of corresponding RNA transcripts as amplicons. Since an RNA polymerase is used, the RNA transcripts are amplicons linearly amplified from the corresponding original double stranded nucleic acid extension product template. The original double stranded nucleic acid extension product is the only template for the corresponding RNA transcript amplicons. The RNA transcripts are not exponential amplicons.

According to one aspect, the RNA transcripts are then reverse transcribed into single stranded DNA. Complementary strands to the single stranded DNA are then made forming double stranded DNA including the genomic DNA sequence and having barcodes at both ends of the upper and lower strands.

According to one aspect, the double stranded DNA including the genomic DNA sequence and having barcodes at both ends of the upper and lower strands are then sequenced using methods known to those of skill in the art.

Embodiments of the present disclosure are directed to a method of amplifying DNA using the methods described herein such as a small amount of genomic DNA or a limited amount of DNA such as a genomic sequence or genomic sequences obtained from a single cell or a plurality of cells of the same cell type or from a tissue, fluid or blood sample obtained from an individual or a substrate. According to certain aspects of the present disclosure, the methods described herein can be performed in a single tube with reactants added thereto under suitable conditions to create DNA amplicons linearly amplified from those genomic DNA fragments. The methods described herein can provide substantial coverage of the entire genome of a single cell producing amplified. DNA for high-throughput sequencing.

According to an additional aspect, methods are provided herein for performing whole genome amplification of single cells with high fidelity and amplification uniformity or coverage across different loci in the genome which is useful for further sequencing or analysis using high throughput sequencing platforms known to those of skill in the art. Methods provided herein minimize amplification bias and provide substantially complete or complete genome coverage of DNA sequencing of genomic DNA from a single cell. Methods described herein can amplify greater than 90 percent of genomic DNA from a single cell while greater than 70 percent or 75 percent of the genomic DNA can be sequenced with a sequencing depth of 7× or 10× or 15× with little, substantially few or no chimera sequences. Methods described herein reduce or eliminate creation of sequencing artifacts and facilitate advanced genomic analysis of single cell single nucleotide polymorphisms, copy number variations and structural variations. Methods described herein have particular application in biological systems or tissue samples characterized by highly heterogeneous cell populations such as tumor and neural masses. Methods described herein to amplify genomic DNA facilitate the analysis of such amplified DNA using next generation sequencing techniques known to those of skill in the art and described herein.

The DNA amplification methods of the present disclosure will be useful for amplifying small or limited amounts of DNA, which will allow multiple sites in the DNA sample to be genotyped for high-throughput screening. Additionally, the present method will allow for the rapid construction of band specific painting probes for any chromosomal region, and can also be used to micro dissect and amplify unidentifiable chromosomal regions or marker chromosomes in abnormal karyotypes. The presently disclosed method will also allow for the rapid cloning of amplified DNA for sequencing or generating DNA libraries. Thus, the method will not only be a valuable tool for genotype analysis and high-throughput screening, it should also be a valuable tool in cytogenetic diagnosis. The methods described herein can utilize varied sources of DNA materials, including genetically heterogeneous tissues (e.g. cancers), rare and precious samples (e.g. embryonic stem cells), and non-dividing cells (e.g. neurons) and the like, as well as, sequencing platforms and genotyping methods known to those of skill in the art.

Further features and advantages of certain embodiments of the present disclosure will become more fully apparent in the following description of the embodiments and drawings thereof, and from the claims.

BRIEF DESCRIPTION OF THE DRAWINGS

The foregoing and other features and advantages of the present invention will be more fully understood from the following detailed description of illustrative embodiments taken in conjunction with the accompanying drawings in which:

FIG. 1 is a schematic of one embodiment of a transposon DNA.

FIG. 8 is a schematic comparing errors resulting from exponential amplification versus linear amplification.

FIG. 9 is a schematic showing different barcodes on genomic DNA fragments.

FIG. 12 is a table summary of the sequencing parameters and results of the amplified DNA from the genomic DNA of a single cell.

DETAILED DESCRIPTION

Figure 2:
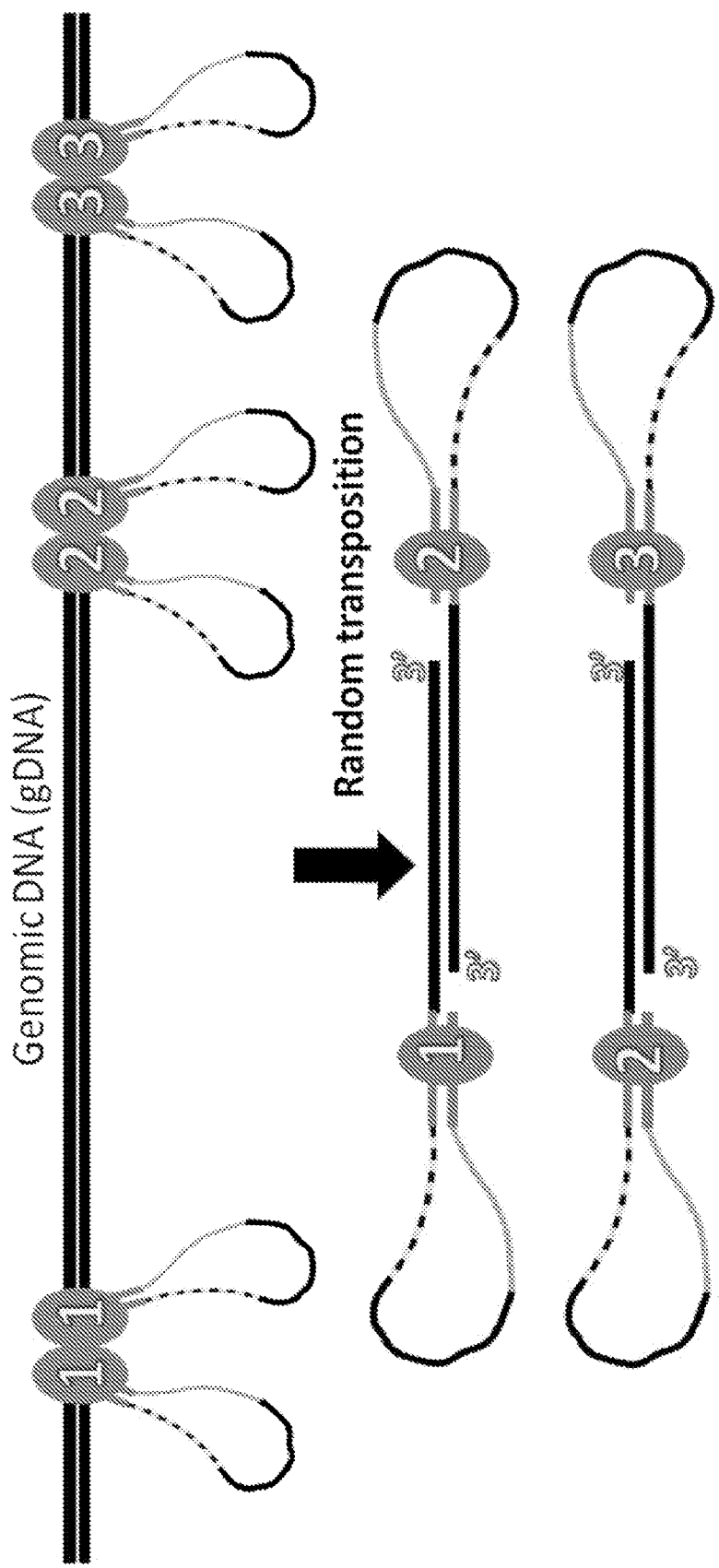
FIG. 2 is a schematic of transposome formation, binding to genomic DNA, cutting and insertion of transposon DNA.

The practice of certain embodiments or features of certain embodiments may employ, unless otherwise indicated, conventional techniques of molecular biology, microbiology, recombinant DNA, and so forth which are within ordinary skill in the art. Such techniques are explained fully in the literature. See e.g., Sambrook, Fritsch, and Maniatis, MOLECULAR CLONING: A LABORATORY MANUAL, Second Edition (1989), OLIGONUCLEOTIDE SYNTHESIS (M. J. Gait Ed., 1984), ANIMAL CELL CULTURE (R. I. Freshney, Ed., 1987), the series METHODS IN ENZYMOLOGY (Academic Press, Inc.); GENE TRANSFER VECTORS FOR MAMMALIAN CELLS (J. M. Miller and M. P. Calos eds. 1987), HANDBOOK OF EXPERIMENTAL IMMUNOLOGY, (D. M. Weir and C. C. Blackwell, Eds.), CURRENT PROTOCOLS IN MOLECULAR BIOLOGY (F. M. Ausubel, R. Brent, R. E. Kingston, D. D. Moore, J. G. Siedman, J. A. Smith, and K. Struhl, eds., 1987), CURRENT PROTOCOLS IN IMMUNOLOGY (J. E. Coligan, A. M. Kruisbeek, D. H. Margulies, E. M. Shevach and W. Strober, eds., 1991); ANNUAL REVIEW OF IMMUNOLOGY; as well as monographs in journals such as ADVANCES IN IMMUNOLOGY. All patents, patent applications, and publications mentioned herein, both supra and infra, are hereby incorporated herein by reference.

Terms and symbols of nucleic acid chemistry, biochemistry, genetics, and molecular biology used herein follow those of standard treatises and texts in the field, e.g., Kornberg and Baker, *DNA Replication*, Second Edition (W.H. Freeman, New York, 1992); Lehninger, *Biochemistry*, Second Edition (Worth Publishers, New York, 1975); Strachan and Read, *Human Molecular Genetics*, Second Edition (Wiley-Liss, New York, 1999); Eckstein, editor, *Oligonucleotides and Analogs: A Practical Approach* (Oxford University Press, New York, 1991); Gait, editor, *Oligonucleotide Synthesis: A Practical Approach* (IRL Press, Oxford, 1984); and the like.

The present invention is based in part on the discovery of methods for making DNA fragment templates, such as from genomic DNA, using a transposase or transposome. The genomic DNA fragment templates may then be amplified and sequenced. DNA fragment templates made using the transposase methods described herein can be amplified using methods known to those of skill in the art. In certain aspects, amplification is achieved using PCR. The term "polymerase chain reaction" ("PCR") of Mullis (U.S. Pat. Nos. 4,683,195, 4,683,202, and 4,965,188) refers to a method for increasing the concentration of a segment of a target sequence in a mixture of nucleic acid sequences without cloning or purification. This process for amplifying the target sequence consists of introducing a large excess of two oligonucleotide primers to the nucleic acid sequence mixture containing the desired target sequence, followed by a precise sequence of thermal cycling in the presence of a polymerase (e.g., DNA polymerase). The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle;" there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of 32P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications. Methods and kits for performing PCR are well known in the art. PCR is a reaction in which replicate copies are made of a target polynucleotide using a pair of primers or a set of primers consisting of an upstream and a downstream primer, and a catalyst of polymerization, such as a DNA polymerase, and typically a thermally-stable polymerase enzyme. Methods for PCR are well known in the art, and taught, for example in MacPherson et al. (1991) PCR 1: A Practical Approach (IRL Press at Oxford University Press). All processes of producing replicate copies of a polynucleotide, such as PCR or gene cloning, are collectively referred to herein as replication. A primer can also be used as a probe in hybridization reactions, such as Southern or Northern blot analyses.

The expression "amplification" or "amplifying" refers to a process by which extra or multiple copies of a particular polynucleotide are formed. Amplification includes methods such as PCR, ligation amplification (or ligase chain reaction, LCR) and other amplification methods. These methods are known and widely practiced in the art. See, e.g., U.S. Pat. Nos. 4,683,195 and 4,683,202 and Innis et al., "PCR protocols: a guide to method and applications" Academic Press, Incorporated (1990) (for PCR); and Wu et al. (1989) Genomics 4:560-569 (for LCR). In general, the PCR procedure describes a method of gene amplification which is comprised of (i) sequence-specific hybridization of primers to specific genes within a DNA sample (or library), (ii) subsequent amplification involving multiple rounds of annealing, elongation, and denaturation using a DNA polymerase, and (iii) screening the PCR products for a band of the correct size. The primers used are oligonucleotides of sufficient length and appropriate sequence to provide initiation of polymerization, i.e. each primer is specifically designed to be complementary to each strand of the genomic locus to be amplified.

Reagents and hardware for conducting amplification reaction are commercially available. Primers useful to amplify sequences from a particular gene region are preferably complementary to, and hybridize specifically to sequences in the target region or in its flanking regions and can be prepared using the polynucleotide sequences provided herein. Nucleic acid sequences generated by amplification can be sequenced directly.

When hybridization occurs in an antiparallel configuration between two single-stranded polynucleotides, the reaction is called "annealing" and those polynucleotides are described as "complementary". A double-stranded polynucleotide can be complementary or homologous to another polynucleotide, if hybridization can occur between one of the strands of the first polynucleotide and the second. Complementarity or homology (the degree that one polynucleotide is complementary with another) is quantifiable in terms of the proportion of bases in opposing strands that are expected to form hydrogen bonding with each other, according to generally accepted base-pairing rules.

The terms "reverse-transcriptase PCR" and "RT-PCR" refer to a type of PCR where the starting material is mRNA. The starting mRNA is enzymatically converted to complementary DNA or "cDNA" using a reverse transcriptase enzyme. The cDNA is then used as a template for a PCR reaction.

The terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

The term "amplification reagents" refers to those reagents (deoxyribonucleotide triphosphates, buffer, etc.), needed for amplification except for primers, nucleic acid template, and the amplification enzyme. Typically, amplification reagents along with other reaction components are placed and contained in a reaction vessel (test tube, microwell, etc.). Amplification methods include PCR methods known to those of skill in the art and also include rolling circle amplification (Blanco et al., J. Biol. Chem., 264, 8935-8940, 1989), hyperbranched rolling circle amplification (Lizard et al., Nat. Genetics, 19, 225-232, 1998), and loop-mediated isothermal amplification (Notomi et al., Nuc. Acids Res., 28, e63, 2000) each of which are hereby incorporated by reference in their entireties.

For emulsion PCR, an emulsion PCR reaction is created by vigorously shaking or stirring a "water in oil" mix to generate millions of micron-sized aqueous compartments. The DNA library is mixed in a limiting dilution either with the beads prior to emulsification or directly into the emulsion mix. The combination of compartment size and limiting dilution of beads and target molecules is used to generate compartments containing, on average, just one DNA molecule and head (at the optimal dilution many compartments will have heads without any target) To facilitate amplification efficiency, both an upstream (low concentration, matches primer sequence on bead) and downstream PCR primers (high concentration) are included in the reaction mix. Depending on the size of the aqueous compartments generated during the emulsification step, up to 3×109 individual PCR reactions per µl can be conducted simultaneously in the same tube. Essentially each little compartment in the emulsion forms a micro PCR reactor. The average size of a compartment in an emulsion ranges from sub-micron in diameter to over a 100 microns, depending on the emulsification conditions.

Other nucleic acid amplification procedures specifically contemplated in the context of the present disclosure include transcription-based amplification systems (rAS), including nucleic acid sequence based amplification (NASBA) and 3SR, Kwoh et aL, Proc Natl Acad Sci USA, 86:1173-77, 1989; PCT Patent Application WO 88/10315 et al., 1989 (each incorporated herein by reference). In NASBA, the nucleic acids can be prepared for amplification by standard phenol/chloroform extraction, heat denaturation of a clinical sample, treatment with lysis buffer, and minispin columns for isolation of DNA and RNA or guanidinium chloride extraction of RNA. These amplification techniques involve annealing a primer which has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by a polymerase such as T7 or SP6. In an isothermal cyclic reaction, the RNAs are reverse transcribed into double stranded DNA, and transcribed once again with a polymerase such as T7 or SP6. The resulting products, whether truncated or complete, indicate target specific sequences.

Other amplification methods, as described in British Patent Application No. GB 2,202,328, and in PCT Patent Application No. PCT/US89/01025, each incorporated herein by reference, may be used in accordance with the present disclosure. In the former application, "modified" primers are used in a PCR-like template and enzyme dependent synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be hound by excess probe. Cleavage of the labeled probe signals the presence of the target sequence.

Davey et al., European Patent Application No. 329,822 (incorporated herein by reference) disclose a nucleic acid amplification process involving cyclically synthesizing single-stranded RNA ("ssRNA"), ssDNA, and double-stranded DNA (dsDNA), which may be used in accordance with the present disclosure. The ssRNA is a first template for a first primer oligonucleotide, which is elongated by reverse transcriptase (RNA-dependent DNA polymerase). The RNA is then removed from the resulting DNA:RNA duplex by the action of ribonuclease H (RNase H, an RNase specific for RNA in duplex with either DNA or RNA). The resultant ssDNA is a second template for a second primer, which also includes the sequences of an RNA polymerase promoter (exemplified by T7 RNA polymerase) 5' of its homology to the template. This primer is then extended by DNA polymerase (exemplified by the large "Klenow" fragment of *E. coli* DNA polymerase I), resulting in a double-stranded DNA molecule, having a sequence identical to that of the original RNA between the primers and having additionally, at one end, a promoter sequence. This promoter sequence can be used by the appropriate RNA polymerase to make many RNA copies of the DNA. These copies can then reenter the cycle leading to very swift amplification. With proper choice of enzymes, this amplification can be done isothermally without adding enzymes at each cycle. Because of the cyclical nature of this process, the starting nucleic acid sequence can be either DNA or RNA.

Miller et al., PCT Patent Application WO 89/06700 (incorporated herein by reference), disclose a nucleic acid sequence amplification scheme based on the hybridization of a promoter/primer sequence to a target single-stranded DNA followed by transcription of many RNA copies of the sequence. This scheme is not cyclic, i.e., new templates are not produced from the resultant RNA transcripts.

Other suitable amplification methods include "race and "one-sided PCR.". (Frohman, In: PCR Protocols: A Guide To Methods And Applications, Academic Press, N.Y., 1990, each herein incorporated by reference). Methods based on ligation of two (or more) oligonucleotides in the presence of nucleic acid having the sequence of the resulting "di-oligonucleotide," thereby amplifying the di-oligonucleotide, also may be used to amplify DNA in accordance with the present disclosure (Wu et al., Genomics 4:560-569, 1989, incorporated herein by reference).

According to one aspect, the DNA fragment templates include an RNA polymerase promoter sequence and an RNA polymerase is used to make RNA amplicons from the DNA fragment templates and a reverse transcriptase to make single stranded DNA from the RNA amplicons. Complements are then made to the single stranded DNA to make double stranded DNA resulting in amplicons linearly amplified from the original DNA fragment template.

According to certain aspects, an exemplary transposon system is a Tn5 transposon system. Other useful transposon systems are known to those of skill in the art and include Tn3 transposon system (see Maekawa, T., Yanagihara, K., and Ohtsubo, E. (1996), A cell-free system of Tn3 transposition and transposition immunity, *Genes Cells* 1, 1007-1016), Tn7 transposon system (see Craig, N. L. (1991), Tn7: a target site-specific transposon, *Mol. Microbiol.* 5, 2569-2573), Tn10 tranposon system (see Chalmers, R., Sewitz, S., Lipkow, K., and Crellin, P. (2000), Complete nucleotide sequence of Tn10, *J. Bacteriol* 182, 2970-2972), Piggybac transposon system (see Li, X., Burnight, E. R., Cooney, A. L, Malani, N., Brady, T., Sander, J. D., Staber, J., Wheelan, S. J., Joung, J. K., McCray, P. B., Jr., et al. (2013), PiggyBac transposase tools for genome engineering, *Proc. Natl. Acad. Sci. USA* 110, E2279-2287), Sleeping beauty transposon system (see Ivies, Z., Hackett, P. B., Piasterk, R. H., and Izsvak, Z. (1997), Molecular reconstruction of Sleeping Beauty, a Tc1-like transposon from fish, and its transposition in human cells, Cell 91, 501-510), Tol2 transposon system (see Kawakami, K. (2007), Tol2: a versatile gene transfer vector in vertebrates, *Genome Biol.* 8 Suppl. 1, S7.)

According to certain aspects, an exemplary RNA polymerase is T7 RNA polymerase. Other useful RNA polymerases are known to those of skill in the art and include T3 RNA polymerase (see Jorgensen, E. D., Durbin, R. K., Risman, S. S., and McAllister, W. T. (1991) Specific contacts between the bacteriophage T3, T7, and SP6 RNA polymerases and their promoters, J. Biol. Chem. 266, 645-651), and SP6 RNA polymerase (see Melton, D. A., Krieg, P. A., Rebagliati, M. R., Maniatis, T., Zinn, K., and Green, M. R. (1984) Efficient in vitro synthesis of biologically active RNA and RNA hybridization probes from plasmids containing a bacteriophage SP6 promoter, *Nucleic Acids Res.* 12, 7035-7056.)

DNA to be amplified may be obtained from a single cell or a small population of cells. Methods described herein allow DNA to be amplified from any species or organism in a reaction mixture, such as a single reaction mixture carried out in a single reaction vessel. In one aspect, methods described herein include sequence independent amplification of DNA from any source including but not limited to human, animal, plant, yeast, viral, eukaryotic and prokaryotic DNA.

According to one aspect, a method of single cell whole genome amplification and sequencing is provided which includes contacting double stranded genomic DNA from a single cell with Tn5 transposases each bound to a transposon DNA, wherein the transposon DNA includes a double-stranded 19 bp transposase (Tnp) binding site and a first nucleic acid sequence including one or more of a barcode sequence, a priming site and an RNA polymerase promoter sequence to form a transposase/transposon DNA complex dimer called a transposome. The first nucleic acid sequence may be in the form of a single stranded extension or the first nucleic acid sequence may be in the form of a loop with each end connected to a corresponding strand of the double stranded transposase binding site. According to one aspect, the first nucleic acid sequence may be an overhang, such as a 5' overhang, wherein the overhang includes a barcode region, a priming site and a strong T7 promoter sequence. The overhang can be of any length suitable to include one or more of a barcode region, a priming site and a strong T7 promoter sequence as desired. The transposome bind to target locations along the double stranded genomic DNA and cleave the double stranded genomic DNA into a plurality of double stranded fragments, with each double stranded fragment having a first complex attached to an upper strand by the Tnp binding site and a second complex attached to a lower strand by the Tnp binding site. The transposon binding site is attached to each 5' end of the double stranded fragment. According to one aspect, the Tn5 transposases are removed from the complex. The double stranded fragments are extended along the transposon DNA to make a double stranded extension product having T7 promoters at each end. According to one aspect, a gap which may result from attachment of the Tn5 transposase binding site to the double stranded genomic DNA fragment may be filled. The double stranded extension product is contacted with T7 RNA polymerase to make an RNA transcript of the double stranded extension product. According to one aspect, a plurality of RNA transcripts of the double stranded extension product are made using T7 RNA polymerase. The RNA transcripts are reverse transcribed into a plurality of corresponding single stranded DNA. Complementary strands to the single stranded DNA are created to form a plurality of double stranded DNA including the genomic DNA sequence and having barcodes at both ends of the upper and lower strands. The plurality of double stranded DNA are amplicons linearly amplified from the corresponding genomic DNA fragments created by the transposases. The double stranded DNA amplicons may then be sequenced using, for example, high-throughput sequencing methods known to those of skill in the art.

In a particular aspect, embodiments are directed to methods for the amplification of substantially the entire genome without loss of representation of specific sites (herein defined as "whole genome amplification"). In a specific embodiment, whole genome amplification comprises simultaneous amplification of substantially all fragments of a genomic library. In a further specific embodiment, "substantially entire" or "substantially all" refers to about 80%, about 85%, about 90%, about 95%, about 97%, or about 99% of all sequence in a genome. A skilled artisan recognizes that amplification of the whole genome will, in some embodiments, comprise non-equivalent amplification of particular sequences over others.

According to one aspect, the DNA sample is genomic DNA, micro dissected chromosome DNA, yeast artificial chromosome (YAC) DNA, cosmid DNA, phage DNA, P1 derived artificial chromosome (PAC) DNA, or bacterial artificial chromosome (BAC) DNA. In another preferred embodiment, the DNA sample is mammalian DNA, plant DNA, yeast. DNA, viral DNA, or prokaryotic DNA. In yet another preferred embodiment, the DNA sample is obtained from a human, bovine, porcine, ovine, equine, rodent, avian, fish, shrimp, plant, yeast, virus, or bacteria. Preferably the DNA sample is genomic DNA.

According to certain exemplary aspects, a transposition system is used to make nucleic acid fragments for amplification and sequencing as desired. According to one particular aspect, a transposition system is combined with an RNA polymerase for single cell genome amplification. According to one aspect, a transposition system is used to fragment genomic DNA into double stranded genomic DNA fragments. An RNA polymerase is used to make RNA amplicons which are then reverse transcribed into DNA. Complements to the DNA are made and double stranded genomic DNA sequences are formed which are amplicons linearly amplified from the original double stranded genomic DNA fragments. According to certain aspects, the use of an RNA polymerase to make amplicons in a linear manner advantageously achieves high quality amplification of the single-cell genomic DNA (gDNA) reducing or avoiding (1) amplification bias, leading to the noisy single-cell sequencing data that further affect the genome coverage, as well as the low resolution detection of copy number variations (CNVs); (2) amplification errors, causing a high false positive rate in the single-cell sequencing data that further prevents the accurate detection of single nucleotide variations (SNVs); and (3) chimera formation during amplification, which overwhelms the signal of structural variations (SVs) from the original single-cell genomic DNA sample. One or more of these aspects can result from exponential amplification such as associated in certain circumstances with PCR amplification. PCR by definition is an exponential amplification method, i.e. new copies are made based on the copies from the previous rounds of amplification. As a result, the slight amplification efficiency difference between amplicons may accumulate, leading to amplification bias between different amplicons after many cycles. In addition, errors made during the early rounds of PCR may propagate further into more copies during the later PCR rounds, which may reduce the overall amplification accuracy after many cycles of amplification.

According to certain aspects when amplifying small amounts of DNA such as DNA from a single cell, a DNA column purification step is not carried out so as to maximize the small amount (~6 pg) of genomic DNA that can be obtained from within a single cell prior to amplification. The DNA can be amplified directly from a cell lysate or other impure condition. Accordingly, the DNA sample may be impure, unpurified, not isolated. Accordingly, aspects of the present method allow one to maximize genomic DNA for amplification and reduce loss due to purification. According to an additional aspect, methods described herein may utilize amplification methods other than PCR, such as an RNA polymerase based amplification method. Such an RNA polymerase-based amplification method as described herein can advantageously reduce the amplification bias and improve the amplification accuracy. For example, a Tn5 transposon DNA is designed to contain a strong T7 promoter sequence. After the transposition reaction, single-cell genomic DNA will be fragmented with each fragment tagged by a strong T7 promoter on both ends, enabling linear amplification afterwards through in vitro transcription.

According to one aspect, transposon DNA is designed to contain a double-stranded 19 bp Tn5 transposase (Tnp) binding site at one end, linked or connected, such as by covalent bond, to a long single-stranded overhang including a barcode region, a priming site, and a strong T7 promoter sequence as shown in FIG. 1. The strong T7 promoter sequence is at the end of the overhang. Upon transposition, the Tnp and the transposon DNA bind to each other and dimerize to form transposomes as shown in FIG. 2. The transposomes then randomly capture or otherwise bind to the target single-cell genomic DNA as dimers as shown in FIG. 2. Representative transposomes are numbered 1-3. Then, the transposases in the transposome cut the genomic DNA with one transposase cutting an upper strand and one transposase cutting a lower strand to create a genomic DNA fragment. The transposon DNA is thus inserted randomly into the single-cell genomic DNA, leaving a 9-bp gap on both ends of the transposition/insertion site. The result is a genomic DNA fragment with a transposon DNA Tnp binding site attached to the 5' position of an upper strand and a transposon DNA Tnp binding site attached to the 5' position of a lower strand. Gaps resulting from the insertion of the transposon DNA are shown.

Figure 3:
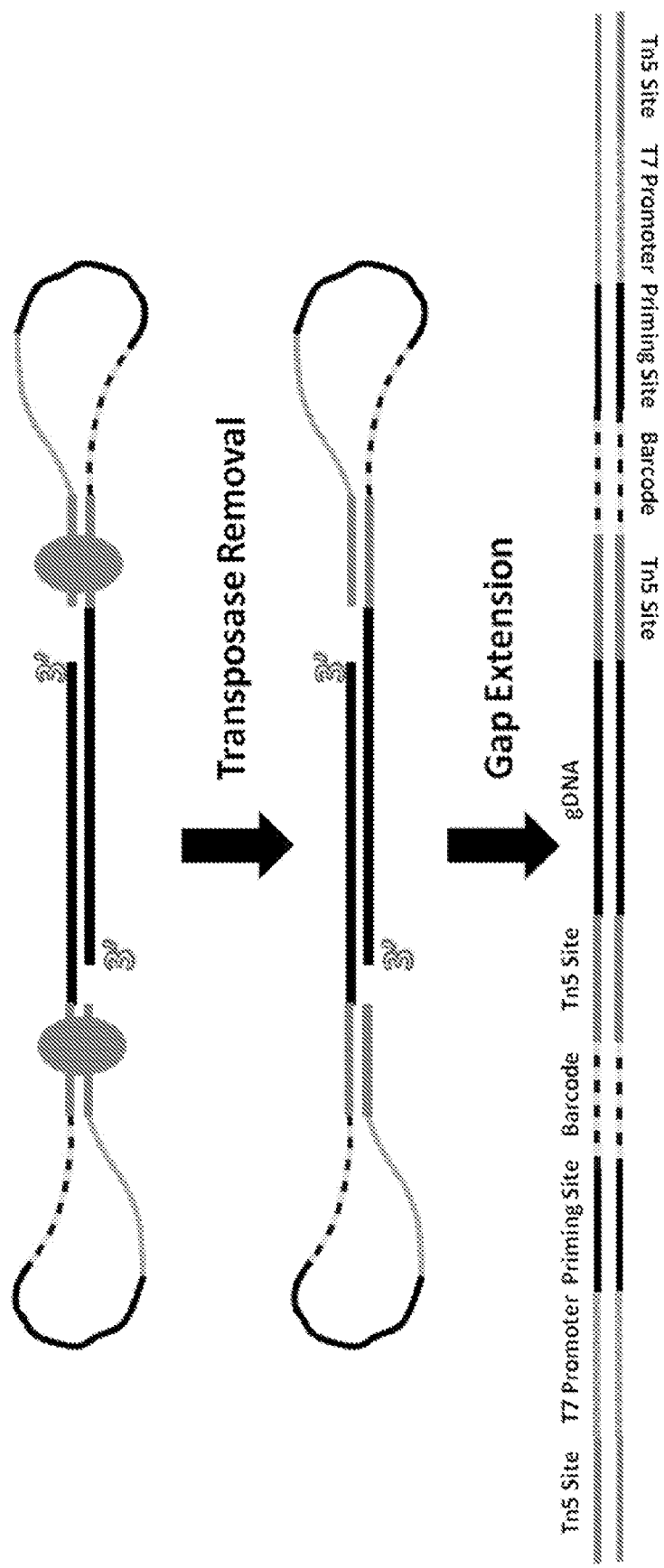
FIG. 3 is a schematic of transposase removal, gap filling and extension to form nucleic acid extension products including genomic DNA.
Figure 4:
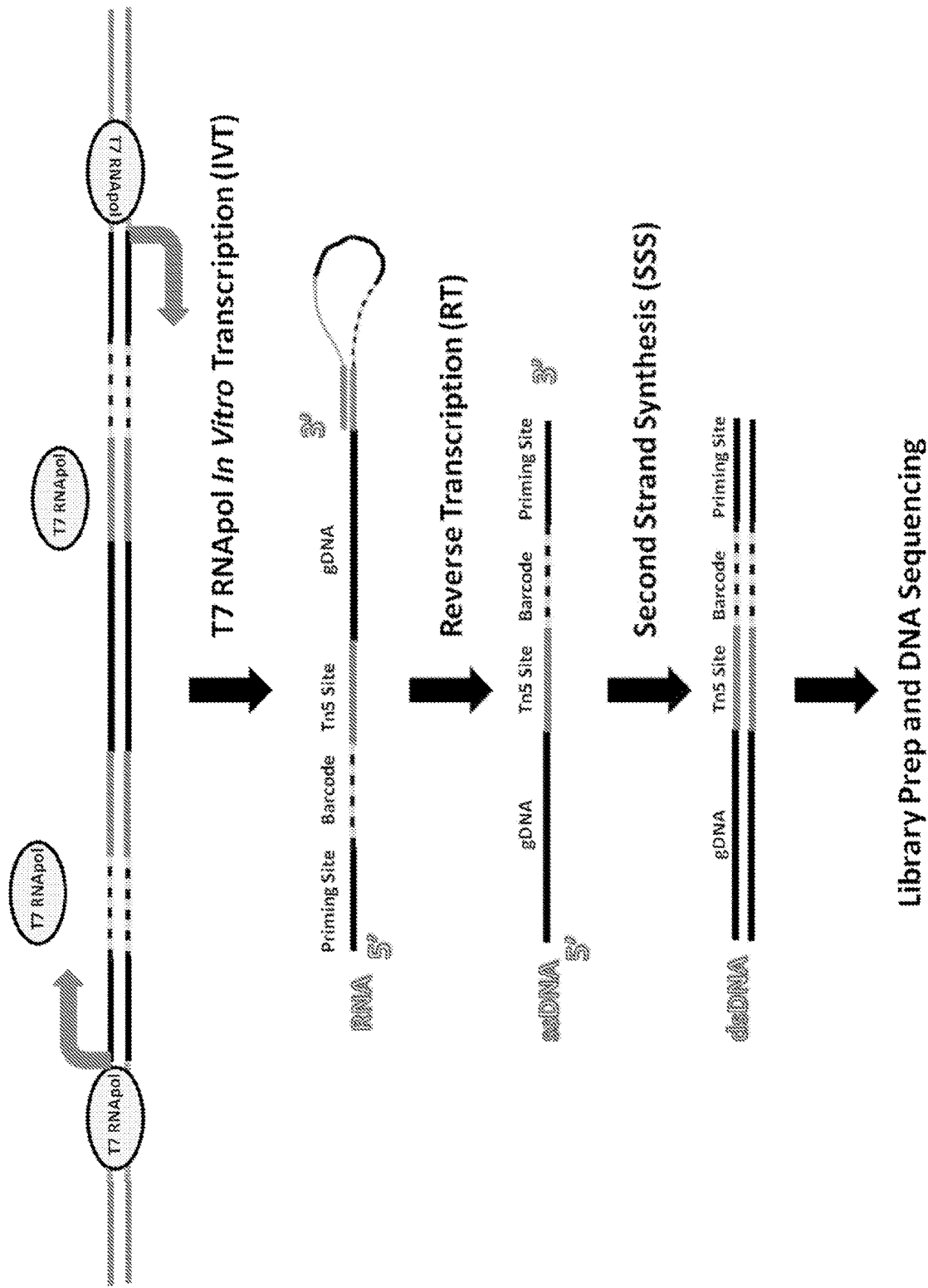
FIG. 4 is a schematic of in vitro transcription, reverse transcription, and second strand synthesis to form double stranded amplicons of DNA fragments.

After transposition, gap extension is performed to fill the 9 bp gap and complement the single-stranded overhang originally designed in the transposon DNA. As a result, active double-stranded T7 promoter sequences are attached to both ends of each genomic DNA fragment as shown in FIG. 3. Next, as shown in FIG. 4, T7 RNA polymerase is added, and in vitro transcription is used to linearly amplify the single-cell genomic DNA fragments, generating many RNAs that contain the same sequence as the original genomic double stranded DNA template. Finally by reverse transcription and second strand synthesis, the amplified RNAs are converted back into double-stranded DNA molecules, with the barcode region originally designed in the transposon DNA attached on both ends of each fragment. The DNA fragments may then be further processed for standard library preparation and sequencing.

Particular Tn5 transposition systems are described and are available to those of skill in the art. See Goryshin, I. Y. and W. S. Reznikoff, *Tn5 in vitro transposition*. The Journal of biological chemistry, 1998. 273(13): p. 7367-74; Davies, D. R., et al., *Three-dimensional structure of the Tn5 synaptic complex transposition intermediate*. Science, 2000. 289 (5476): p. 77-85; Goryshin, I. Y., et al., *Insertional transposon mutagenesis by electroporation of released Tn5transposition complexes*. Nature biotechnology, 2000. 18(1): p. 97-100 and Steiniger-White, M., I. Rayment, and W. S. Reznikoff, Structure/function insights into Tn5 transposition. Current opinion in structural biology, 2004. 14(1): p. 50-7 each of which are hereby incorporated by reference in their entireties for all purposes. Kits utilizing a Tn5 transposition system for DNA library preparation and other uses are known. See Adey, A., et al., *Rapid, low-input, low-bias construction of shotgun fragment libraries by high-density in vitro transposition*. Genome biology, 2010. 11(12): p. R119; Marine, R., et al., *Evaluation of a transposase protocol for rapid generation of shotgun high-throughput sequencing libraries from nanogram quantities of DNA*. Applied and environmental microbiology, 2011. 77(22): p. 8071-9; Parkinson, N. J., et al., *Preparation of high-quality next-generation sequencing libraries from picogram quantities of target DNA*, Genome research, 2012. 22(1): p. 125-33; Adey, A. and J. Shendure, *Ultra-low-input, tagmentation-based whole-genome bisulfite sequencing*. Genome research, 2012. 22(6): p. 1139-43; Picelli, S., et al., *Full-length RNA-seq from single cells using Smart-seq2*. Nature protocols, 2014. 9(1): p. 171-81 and Buenrostro, et al., *Transposition of native chromatin for fast and sensitive epigenomic profiling of open chromatin, DNA-binding proteins and nucleosome position*. Nature methods, 2013, each of which are hereby incorporated by reference in their entireties for all purposes. See also WO 98/10077, EP 2527438 and EP 2376517 each of which are hereby incorporated by reference in their entireties. A commercially available transposition kit is marketed under the name NEXTERA and is available from Illumina.

In vitro transcription (IVT) by T7 RNA polymerase is useful to create RNA amplicons. See Van Gelder, R. N., et al., Amplified RNA synthesized from limited quantities of heterogeneous cDNA. Proceedings of the National Academy of Sciences of the United States of America, 1990. 87(5): p. 1663-7; Kawasaki, E. S., Microarrays and the gene expression profile of a single cell. Annals of the New York Academy of Sciences, 2004, 1020: p. 92-1.00; Livesey, F. J., Strategies for microarray analysis of limiting amounts of RNA. Briefings in functional genomics & proteomics, 2003. 2(1): p. 31-6; Tang, F., K. Lao, and M. A. Sunni, Development and applications of single-cell transcriptome analysis. Nature methods, 2011. 8(4 Suppl): p. S6-11; Hashimshony, T., et al., CEL-Seq: single-cell RNA-Seq by multiplexed linear amplification. Cell reports, 2012. 2(3): p. 666-73; and Shankaranarayanan, P., et al., Single-tube linear DNA amplification for genome-wide studies using a few thousand cells. Nature protocols, 2012. 7(2): p. 328-38 each of which are hereby incorporated by reference in their entireties. According to the present disclosure, IVT advantageously provides linear amplification, with all the copies generated from the original DNA template. The resulting RNA molecules can be reverse transcribed into single stranded DNA followed by complementary strand formation resulting in double stranded DNA, which are amplicons linearly amplified from the original DNA template. As a result of the use of an RNA polymerase for linear amplification, amplification bias is much smaller between different amplicons. Moreover, amplification accuracy is higher since in linear amplification the amplification errors cannot propagate into later stages. According to certain aspects, an RNA promoter sequence is attached to target DNA to advantageously use an RNA polymerase, such as T7 RNA polymerase, to create RNA amplicons which are then used to create DNA amplicons of the original DNA template.

According to one aspect, the method of amplifying DNA further includes genotype analysis of the amplified DNA product. Alternatively, the method of amplifying DNA preferably further includes identifying a polymorphism such as a single nucleotide polymorphism (SNP) in the amplified DNA product. In preferred embodiments, a SNP may be identified in the DNA of an organism by a number of methods well known to those of skill in the art, including but not limited to identifying the SNP by DNA sequencing, by amplifying a PCR product and sequencing the PCR product, by Oligonucleotide Ligation Assay (OLA), by Doublecode OLA, by Single Base Extension Assay, by allele specific primer extension, or by mismatch hybridization. Preferably the identified SNP is associated with a phenotype, including disease phenotypes and desirable phenotypic traits. The amplified DNA generated by using the disclosed method of DNA amplification may also preferably be used to generate a DNA library, including but not limited to genomic DNA libraries, microdissected chromosome DNA libraries, BAC libraries, YAC libraries, PAC libraries, cDNA libraries, phage libraries, and cosmid libraries.

The term "genome" as used herein is defined as the collective gene set carried by an individual, cell, or organelle. The term "genomic DNA" as used herein is defined as DNA material comprising the partial or full collective gene set carried by an individual, cell, or organelle.

As used herein, the term "nucleoside" refers to a molecule having a purine or pyrimidine base covalently linked to a ribose or deoxyribose sugar. Exemplary nucleosides include adenosine, guanosine, cytidine, uridine and thymidine. Additional exemplary nucleosides include inosine, 1-methyl inosine, pseudouridine, 5,6-dihydrouridine, ribothymidine, 2N-methylguanosine and 2,2N,N-dimethylguanosine (also referred to as "rare" nucleosides). The term "nucleotide" refers to a nucleoside having one or more phosphate groups joined in ester linkages to the sugar moiety. Exemplary nucleotides include nucleoside monophosphates, diphosphates and triphosphates. The terms "polynucleotide," "oligonucleotide" and "nucleic acid molecule" are used interchangeably herein and refer to a polymer of nucleotides, either deoxyribonucleotides or ribonucleotides, of any length joined together by a phosphodiester linkage between 5' and 3' carbon atoms. Polynucleotides can have any three-dimensional structure and can perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. The term also refers to both double- and single-stranded molecules. Unless otherwise specified or required, any embodiment of this invention that comprises a polynucleotide encompasses both the double-stranded form and each of two complementary single-stranded forms known or predicted to make up the double-stranded form. A polynucleotide is composed of a specific sequence of four nucleotide bases: adenine (A); cytosine (C); guanine (G); thymine (T); and uracil (U) for thymine when the polynucleotide is RNA. Thus, the term polynucleotide sequence is the alphabetical representation of a polynucleotide molecule. This alphabetical representation can be input into databases in a computer having a central processing unit and used for bioinformatics applications such as functional genomics and homology searching.

The terms "RNA," "RNA molecule" and "ribonucleic acid molecule" refer to a polymer of ribonucleotides. The terms "DNA," "DNA molecule" and "deoxyribonucleic acid molecule" refer to a polymer of deoxyribonucleotides. DNA and RNA can be synthesized naturally (e.g., by DNA replication or transcription of DNA, respectively). RNA can be post-transcriptionally modified. DNA and RNA can also be chemically synthesized. DNA and RNA can be single-stranded (i.e., ssRNA and ssDNA, respectively) or multi-stranded (e.g., double stranded, i.e., dsRNA and dsDNA, respectively).

The terms "nucleotide analog," "altered nucleotide" and "modified nucleotide" refer to a non-standard nucleotide, including non-naturally occurring ribonucleotides or deoxyribonucleotides. In certain exemplary embodiments, nucleotide analogs are modified at any position so as to alter certain chemical properties of the nucleotide yet retain the ability of the nucleotide analog to perform its intended function. Examples of positions of the nucleotide which may be derivitized include the 5 position, e.g., 5-(2-amino)propyl uridine, 5-bronco uridine, 5-propyne uridine, 5-propenyl uridine, etc.; the 6 position, e.g., 6-(2-amino) propyl uridine; the 8-position for adenosine and/or guanosines, e.g., 8-bromo guanosine, 8-chloro guanosine, 8-fluoroguanosine, etc. Nucleotide analogs also include deaza nucleotides, e.g., 7-deaza-adenosine; O- and N-modified (e.g., alkylated, e.g., N6-methyl adenosine, or as otherwise known in the art) nucleotides; and other heterocyclically modified nucleotide analogs such as those described in Herdewijn, Antisense Nucleic Acid Drug Dev., 2000 Aug. 10(4):297-310.

Nucleotide analogs may also comprise modifications to the sugar portion of the nucleotides. For example the 2' OH-group may be replaced by a group selected from H, OR, R, F, Cl, Br, I, SH, SR, NH$_2$, NHR, NR$_2$, COOR, or OR, wherein R is substituted or unsubstituted $C_1$-$C_6$ alkyl, alkenyl, alkynyl, aryl, etc. Other possible modifications include those described in U.S. Pat. Nos. 5,858,988, and 6,291,438.

The phosphate group of the nucleotide may also be modified, e.g., by substituting one or more of the oxygens of the phosphate group with sulfur (e.g., phosphorothioates), or by making other substitutions which allow the nucleotide to perform its intended function such as described in, for example, Eckstein, Antisense Nucleic Acid Drug Dev. 2000 Apr. 10(2):117-21, Rusckowski et al. Antisense Nucleic Acid Drug Dev. 2000 Oct. 10(5):333-45, Stein, Antisense Nucleic Acid Drug Dev. 2001 Oct. 11(5): 317-25, Vorobjev et al. Antisense Nucleic Acid Drug Dev. 2001 Apr. 11(2): 77-85, and U.S. Pat. No. 5,684,143. Certain of the above-referenced modifications (e.g., phosphate group modifications) decrease the rate of hydrolysis of, for example, polynucleotides comprising said analogs in vivo or in vitro.

The term "in vitro" has its art recognized meaning, e.g., involving purified reagents or extracts, e.g., cell extracts. The term "in vivo" also has its art recognized meaning, e.g., involving living cells, e.g., immortalized cells, primary cells, cell lines, and/or cells in an organism.

As used herein, the terms "complementary" and "complementarity" are used in reference to nucleotide sequences related by the base-pairing rules. For example, the sequence 5'-AGT-3' is complementary to the sequence 5'-ACT-3'. Complementarity can be partial or total. Partial complementarity occurs when one or more nucleic acid bases is not matched according to the base pairing rules. Total or complete complementarity between nucleic acids occurs when each and every nucleic acid base is matched with another base under the base pairing rules. The degree of complementarily between nucleic acid strands has significant effects on the efficiency and strength of hybridization between nucleic acid strands.

The term "hybridization" refers to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

The term "$T_m$" refers to the melting temperature of a nucleic acid. The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m$=81.5+0.41 (% G+C), when a nucleic acid is in aqueous solution at 1 M NaCl (See, e.g., Anderson and Young, Quantitative Filter Hybridization, in *Nucleic Acid Hybridization* (1985)). Other references include more sophisticated computations that take structural as well as sequence characteristics into account for the calculation of $T_m$.

The term "stringency" refers to the conditions of temperature, ionic strength, and the presence of other compounds such as organic solvents, under which nucleic acid hybridizations are conducted.

"Low stringency conditions," when used in reference to nucleic acid hybridization, comprise conditions equivalent to binding or hybridization at 42° C. in a solution consisting of 5×SPE (43.8 g/l NaCl, 6.9 g/l NaH$_2$PO$_4$(H$_2$O) and 1.85 g/l EDTA, pH adjusted to 7.4 with NaOH), 0.1% SDS, 5× Denhardt's reagent (50× Denhardt's contains per 500 ml: 5 g Ficoll (Type 400, Pharmacia), 5 g BSA (Fraction V; Sigma)) and 100 □g/ml denatured salmon sperm DNA followed by washing in a solution comprising 5× SSPE, 0.1% SDS at 42° C. when a probe of about 500 nucleotides in length is employed.

"Medium stringency conditions," when used in reference to nucleic acid hybridization, comprise conditions equivalent to binding or hybridization at 42° C. in a solution consisting of 5×SSPE (43.8 g/l NaCl, 6.9 g/l NaH$_2$PO$_4$(H$_2$O) and 1.85 g/l EDTA, pH adjusted to 7.4 with NaOH), 0.5% SDS, 5× Denhardt's reagent and 100 □g/ml denatured salmon sperm DNA followed by washing in a solution comprising 1.0×SSPE, 1.0% SDS at 42° C. when a probe of about 500 nucleotides in length is employed.

"High stringency conditions," when used in reference to nucleic acid hybridization, comprise conditions equivalent to binding or hybridization at 42° C. in a solution consisting of 5× SSPE (43.8 g/l NaCl, 6.9 g/l NaH$_2$PO$_4$(H$_2$O) and 1.85 g/l EDTA, pH adjusted to 7.4 with NaOH), 0.5% SDS, 5× Denhardt's reagent and 100 □g/l denatured salmon sperm DNA followed by washing in a solution comprising 0.1× SSPE, 1.0% SDS at 42° C. when a probe of about 500 nucleotides in length is employed.

In certain exemplary embodiments, cells are identified and then a single cell or a plurality of cells are isolated. Cells within the scope of the present disclosure include any type of cell where understanding the DNA content is considered by those of skill in the art to be useful. A cell according to the present disclosure includes a cancer cell of any type, hepatocyte, oocyte, embryo, stem cell, iPS cell, ES cell, neuron, erythrocyte, melanocyte, astrocyte, germ cell, oligodendrocyte, kidney cell and the like. According to one aspect, the methods of the present invention are practiced with the cellular DNA from a single cell. A plurality of cells includes from about 2 to about 1,000,000 cells, about 2 to about 10 cells, about 2 to about 100 cells, about 2 to about 1,000 cells, about 2 to about 10,000 cells, about 2 to about 100,000 cells, about 2 to about 10 cells or about 2 to about 5 cells.

Nucleic acids processed by methods described herein may be DNA and they may be obtained from any useful source, such as, for example, a human sample. In specific embodiments, a double stranded DNA molecule is further defined as comprising a genome, such as, for example, one obtained from a sample from a human. The sample may be any sample from a human, such as blood, serum, plasma, cerebrospinal fluid, cheek scrapings, nipple aspirate, biopsy, semen (which may be referred to as ejaculate), urine, feces, hair follicle, saliva, sweat, immunoprecipitated or physically isolated chromatin, and so forth. In specific embodiments, the sample comprises a single cell.

In particular embodiments, the amplified nucleic acid molecule from the sample provides diagnostic or prognostic information. For example, the prepared nucleic acid molecule from the sample may provide genomic copy number and/or sequence information, allelic variation information, cancer diagnosis, prenatal diagnosis, paternity information, disease diagnosis, detection, monitoring, and/or treatment information, sequence information, and so forth.

As used herein, a "single cell" refers to one cell. Single cells useful in the methods described herein can be obtained from a tissue of interest, or from a biopsy, blood sample, or cell culture. Additionally, cells from specific organs, tissues, tumors, neoplasms, or the like can be obtained and used in the methods described herein. Furthermore, in general, cells from any population can be used in the methods, such as a population of prokaryotic or eukaryotic single celled organisms including bacteria or yeast. A single cell suspension can be obtained using standard methods known in the art including, for example, enzymatically using trypsin or papain to digest proteins connecting cells in tissue samples or releasing adherent cells in culture, or mechanically separating cells in a sample. Single cells can be placed in any suitable reaction vessel in which single cells can be treated individually. For example a 96-well plate, such that each single cell is placed in a single well.

Methods for manipulating single cells are known in the art and include fluorescence activated cell sorting (FACS), flow cytometry (Herzenberg, PNAS USA 76:1453-55 1979), micromanipulation and the use of semi-automated cell pickers (e.g. the Quixell™ cell transfer system from Stoelting Co.). Individual cells can, for example, be individually selected based on features detectable by microscopic observation, such as location, morphology, or reporter gene expression. Additionally, a combination of gradient centrifugation and flow cytometry can also be used to increase isolation or sorting efficiency.

Once a desired cell has been identified, the cell is lysed to release cellular contents including DNA, using methods known to those of skill in the art. The cellular contents are contained within a vessel. In some aspects of the invention, cellular contents, such as genomic DNA, can be released from the cells by lysing the cells. Lysis can be achieved by, for example, heating the cells, or by the use of detergents or other chemical methods, or by a combination of these. However, any suitable lysis method known in the art can be used. For example, heating the cells at 72° C. for 2 minutes in the presence of Tween-20 is sufficient to lyse the cells. Alternatively, cells can be heated to 65° C. for 10 minutes in water (Esumi et al., *Neurosci Res* 60(4):439-51 (2008)); or 70° C. for 90 seconds in PCR buffer H (Applied Biosystems) supplemented with 0.5% NP-40 (Kurimoto et al., *Nucleic Acids Res* 34(5):e42 (2006)); or lysis can be achieved with a protease such as Proteinase K or by the use of chaotropic salts such as guanidine isothiocyanate (U.S. Publication No. 2007/0281313). Amplification of genomic DNA according to methods described herein can be performed directly on cell lysates, such that a reaction mix can be added to the cell lysates. Alternatively, the cell lysate can be separated into two or more volumes such as into two or more containers, tubes or regions using methods known to those of skill in the art with a portion of the cell lysate contained in each volume container, tube or region. Genomic DNA contained in each container, tube or region may then be amplified by methods described herein or methods known to those of skill in the art.

A nucleic acid used in the invention can also include native or non-native bases. In this regard a native deoxyribonucleic acid can have one or more bases selected from the group consisting of adenine, thymine, cytosine or guanine and a ribonucleic acid can have one or more bases selected from the group consisting of uracil, adenine, cytosine or guanine. Exemplary non-native bases that can be included in a nucleic acid, whether having a native backbone or analog structure, include, without limitation, inosine, xathanine, hypoxathanine, isocytosine, isoguanine, 5-methylcytosine, 5-hydroxymethyl cytosine, 2-aminoadenine, 6-methyl adenine, 6-methyl guanine, 2-propyl guanine, 2-propyl adenine, 2-thioLiracil, 2-thiothymine, 2-thiocytosine, 15-halouracil, 15-halocytosine, 5-propynyl uracil, 5-propynyl cytosine, 6-azo uracil, 6-azo cytosine, 6-azo thymine, 5-uracil, 4-thiouracil, 8-halo adenine or guanine, 8-amino adenine or guanine, 8-thiol adenine or guanine, 8-thioalkyl adenine or guanine, 8-hydroxyl adenine or guanine, 5-halo substituted uracil or cytosine, 7-methylguanine, 7-methyladenine, 8-azaguanine, 8-azaadenine, 7-deazaguanine, 7-deazaadenine, 3-deazaguanine, 3-deazaadenine or the like. A particular embodiment can utilize isocytosine and isoguanine in a nucleic acid in order to reduce non-specific hybridization, as generally described in U.S. Pat. No. 5,681,702.

As used herein, the term "primer" generally includes an oligonucleotide, either natural or synthetic, that is capable, upon forming a duplex with a polynucleotide template, of acting as a point of initiation of nucleic acid synthesis, such as a sequencing primer, and being extended from its 3' end along the template so that an extended duplex is formed. The sequence of nucleotides added during the extension process is determined by the sequence of the template polynucleotide. Usually primers are extended by a DNA polymerase. Primers usually have a length in the range of between 3 to 36 nucleotides, also 5 to 24 nucleotides, also from 14 to 36 nucleotides. Primers within the scope of the invention include orthogonal primers, amplification primers, constructions primers and the like. Pairs of primers can flank a sequence of interest or a set of sequences of interest. Primers and probes can be degenerate or quasi-degenerate in sequence. Primers within the scope of the present invention bind adjacent to a target sequence. A "primer" may be considered a short polynucleotide, generally with a free 3' —OH group that binds to a target or template potentially present in a sample of interest by hybridizing with the target, and thereafter promoting polymerization of a polynucleotide complementary to the target. Primers of the instant invention are comprised of nucleotides ranging from 17 to 30 nucleotides. In one aspect, the primer is at least 17 nucleotides, or alternatively, at least 18 nucleotides, or alternatively, at least 19 nucleotides, or alternatively, at least 20 nucleotides, or alternatively, at least 21 nucleotides, or alternatively, at least 22 nucleotides, or alternatively, at least 23 nucleotides, or alternatively, at least 24 nucleotides, or alternatively, at least 25 nucleotides, or alternatively, at least 26 nucleotides, or alternatively, at least 27 nucleotides, or alternatively, at least 28 nucleotides, or alternatively, at least 29 nucleotides, or alternatively, at least 30 nucleotides, or alternatively at least 50 nucleotides, or alternatively at least 75 nucleotides or alternatively at least 100 nucleotides.

The expression "amplification" or "amplifying" refers to a process by which extra or multiple copies of a particular polynucleotide are formed.

The terms "reverse-transcriptase PCR" and "RT-PCR" refer to a type of PCR where the starting material is mRNA. The starting mRNA is enzymatically converted to complementary DNA or "cDNA" using a reverse transcriptase enzyme.

The DNA amplified according to the methods described herein may be sequenced and analyzed using methods known to those of skill in the art. Determination of the sequence of a nucleic acid sequence of interest can be performed using a variety of sequencing methods known in the art including, but not limited to, sequencing by hybridization (SBH), sequencing by ligation (SBL) (Shendure et al. (2005) *Science* 309:1728), quantitative incremental fluorescent nucleotide addition sequencing (QIFNAS), stepwise ligation and cleavage, fluorescence resonance energy transfer (FRET), molecular beacons, TaqMan reporter probe digestion, pyrosequencing, fluorescent in situ sequencing (FISSEQ), FISSEQ beads (U.S. Pat. No. 7,425,431), wobble sequencing (PCT/US05/27695), multiplex sequencing (U.S. Ser. No. 12/027,039, filed Feb. 6, 2008; Porreca et al (2007) *Nat. Methods* 4:931), polymerized colony (POLONY) sequencing (U.S. Pat. Nos. 6,432,360, 6,485,944 and 6,511,803, and PCT/US05/06425); nanogrid rolling circle sequencing (ROLONY) (U.S. Ser. No. 12/120,541, filed May 14, 2008), allele-specific oligo ligation assays (e.g., oligo ligation assay (OLA), single template molecule OLA using a ligated linear probe and a rolling circle amplification (RCA) readout, ligated padlock probes, and/or single template molecule OLA using a ligated circular padlock probe and a rolling circle amplification (RCA) readout) and the like. High-throughput sequencing methods, e.g., using platforms such as Roche 454, Illumina Solexa, AB-SOUL), Helicos, Polonator platforms and the like, can also be utilized. A variety of light based sequencing technologies are known in the art (Landegren et al. (1998) *Genome Res.* 8:769-76; Kwok (2000) *Pharmacogenomics* 1:95-100; and Shi (2001) *Clin. Chem.* 47:164-172).

The amplified DNA can be sequenced by any suitable method. In particular, the amplified DNA can be sequenced using a high-throughput screening method, such as Applied Biosystems' SOLID sequencing technology, or Illumina's Genome Analyzer. In one aspect of the invention, the amplified DNA can be shotgun sequenced. The number of reads can be at least 10,000, at least 1 million, at least 10 million, at least 100 million, or at least 1000 million. In another aspect, the number of reads can be from 10,000 to 100,000, or alternatively from 100,000 to 1 million, or alternatively from 1 million to 10 million, or alternatively from 10 million to 100 million, or alternatively from 100 million to 1000 million. A "read" is a length of continuous nucleic acid sequence obtained by a sequencing reaction.

"Shotgun sequencing" refers to a method used to sequence very large amount of DNA (such as the entire genome). In this method, the DNA to be sequenced is first shredded into smaller fragments which can be sequenced individually. The sequences of these fragments are then reassembled into their original order based on their overlapping sequences, thus yielding a complete sequence. "Shredding" of the DNA can be done using a number of difference techniques including restriction enzyme digestion or mechanical shearing. Overlapping sequences are typically aligned by a computer suitably programmed Methods and programs for shotgun sequencing a cDNA library are well known in the art.

The amplification and sequencing methods are useful in the field of predictive medicine in which diagnostic assays, prognostic assays, pharmacogenomics, and monitoring clinical trials are used for prognostic (predictive) purposes to thereby treat an individual prophylactically. Accordingly, one aspect of the present invention relates to diagnostic assays for determining the genomic DNA in order to determine whether an individual is at risk of developing a disorder and/or disease. Such assays can be used for prognostic or predictive purposes to thereby prophylactically treat an individual prior to the onset of the disorder and/or disease. Accordingly, in certain exemplary embodiments, methods of diagnosing and/or prognosing one or more diseases and/or disorders using one or more of expression profiling methods described herein are provided.

As used herein, the term "biological sample" is intended to include, but is not limited to, tissues, cells, biological fluids and isolates thereof, isolated from a subject, as well as tissues, cells and fluids present within a subject.

In certain exemplary embodiments, electronic apparatus readable media comprising one or more genomic DNA sequences described herein is provided. As used herein, "electronic apparatus readable media" refers to any suitable medium for storing, holding or containing data or information that can be read and accessed directly by an electronic apparatus. Such media can include, but are not limited to: magnetic storage media, such as floppy discs, hard disc storage medium, and magnetic tape; optical storage media such as compact disc; electronic storage media such as RAM, ROM, EPROM, EEPROM and the like; general hard disks and hybrids of these categories such as magnetic/optical storage media. The medium is adapted or configured for having recorded thereon one or more expression profiles described herein.

As used herein, the term "electronic apparatus" is intended to include any suitable computing or processing apparatus or other device configured or adapted for storing data or information. Examples of electronic apparatuses suitable for use with the present invention include standalone computing apparatus; networks, including a local area network (LAN), a wide area network (WAN) Internet, Intranet, and Extranet; electronic appliances such as a personal digital assistants (PDAs), cellular phone, pager and the like; and local and distributed processing systems.

As used herein, "recorded" refers to a process for storing or encoding information on the electronic apparatus readable medium. Those skilled in the art can readily adopt any of the presently known methods for recording information on known media to generate manufactures comprising one or more expression profiles described herein.

A variety of software programs and formats can be used to store the genomic DNA information of the present invention on the electronic apparatus readable medium. For example, the nucleic acid sequence can be represented in a word processing text file, formatted in commercially-available software such as WordPerfect and MicroSoft Word, or represented in the form of an ASCII file, stored in a database application, such as DB2, Sybase, Oracle, or the like, as well as in other forms. Any number of data processor structuring formats (e.g., text file or database) may be employed in order to obtain or create a medium having recorded thereon one or more expression profiles described herein.

It is to be understood that the embodiments of the present invention which have been described are merely illustrative of some of the applications of the principles of the present invention. Numerous modifications may be made by those skilled in the art based upon the teachings presented herein without departing from the true spirit and scope of the invention. The contents of all references, patents and published patent applications cited throughout this application are hereby incorporated by reference in their entirety for all purposes.

The following examples are set forth as being representative of the present invention. These examples are not to be construed as limiting the scope of the invention as these and other equivalent embodiments will be apparent in view of the present disclosure, figures and accompanying claims.

Example I

Combining Transposase with Transposon DNA

Tn5 transposase (Epicentre) is mixed with transposon DNA in equal molar number in a buffer containing EDTA and incubated at room temperature for 10-60 minutes. The final transposome concentration is 0.1-10 µM. The transposon DNA construct could be linear or looped form, with a double stranded 19 bp transposase binding site on one end, and single stranded T7 promoter on the other end. In the linear form, the single-stranded T7 promoter sequence forms a 5' protruding end; while in the looped form, the single-stranded T7 promoter sequence forms a loop and connects both strands of the 19 bp binding site. Barcode sequences with variable length and sequence complexity could be designed as needed between the 19 bp binding site and the T7 promoter sequence, together with a specific priming region between the barcodes and the T7 promoter. The transposome may be diluted by many folds in 50% Tris-EDTA and 50% glycerol solution and preserved at −20° C.

Example II

Cell Lysis

A cell is selected, cut from a culture dish, and dispensed in a tube using a laser dissection microscope (LMD-6500, Leica) as follows. The cells are plated onto a membrane-coated culture dish and observed using bright field microscopy with a 10× objective (Leica). A UV laser is then used to cut the membrane around an individually selected cell such that it falls into the cap of a PCR tube. The tube is briefly centrifuged to bring the cell down to the bottom of the tube. 3-5 µl lysis buffer (30 mM Tris-Cl PH 7.8, 2 mM EDTA, 20 mM KCl, 0.2% Triton X-100, 500 µg/ml Qiagen Protease) is added to the side of the PCR tube and span down. The captured cell is then thermally lysed using the using following temperature schedule on PCR machine: 50° C. 3 hours, 75° C. 30 minutes. Alternatively, mouth pipette a single cell into a low salt lysis buffer containing EDTA and protease such as QIAGEN protease (QIAGEN) at a concentration of 10-5000 µg/mL. The incubation condition varies based on the protease that is used. In the case of QIAGEN protease, the incubation would be 37-55° C. for 1-4 hrs. The protease is then heat inactivated up to 80° C. and further inactivated by specific protease inhibitors such as 4-(2-Aminoethyl) benzenesulfonyl fluoride hydrochloride (AEBSF) or phenylmethanesulfonyl fluoride (PMSF) (Sigma Aldrich). The cell lysis is preserved at −80° C.

Example III

Transposition

The single cell lysis and the transposome are mixed in a buffer system containing 1-100 mM $Mg^{2+}$ and optionally 1-100 mM $Mn^{2+}$ or $Co^{2+}$ or $Ca^{2+}$ as well. Mix well and incubate at 37-55° C. for 5-240 minutes. The reaction volume varies depending on the cell lysis volume. The amount of transposome added in the reaction could be readily tuned depending on the desired fragmentation size. The transposition reaction is stopped by chelating $Mg^{2+}$ using EDTA and optionally EGTA or other chelating agents for ions. The residue transposome is inactivated by protease digestion such as QIAGEN protease at a final concentration 1-500 µg/mL at 37-55° C. for 10-60 minutes. The protease is then inactivated by heat and/or protease inhibitor.

Example IV

Gap Filling

After transposition, $Mg^{2+}$ is added to the solution. dNTP mix and DNA polymerase such as Bst 2.0 Warm Start DNA polymerase (New England Biolabs) are added to fill the 9 bp gap left by the transposition reaction and to extend all the way down to both ends of each fragment to make the T7 promoter double-stranded and thus active. The gap filling incubation temperature and time depends on the specific DNA polymerase used. After the reaction, the DNA polymerase is optionally inactivated by heating and/or protease treatment such as QIAGEN protease. The protease, if used, is then inactivated by heat and/or protease inhibitor.

Example V

In Vitro Transcription Linear Amplification

The in vitro transcription assay is assembled by adding in vitro transcription assay components to the gap filling mixture, including T7 RNA polymerase (New England Biolabs or Epicentre), NTP mixture, and T7 transcription buffer containing $Mg^{2+}$ and DTT. Optionally RNase Inhibitors such as Superase (Life Technologies) and optionally inorganic pyrophosphatase (New England Biolabs) could be added. The T7 in vitro transcription linear amplification reaction could be 1 hr up to 16 hrs at 37° C., in a volume between 20 uL to 200 uL.

Example VI

Reverse Transcription and Second Strand Synthesis

After the transcription, RNA is column purified (Zymo Research or QIAGEN). Optionally DNase I (New England Biolabs) treatment could be carried out as an additional purification step. Reverse transcription is performed by reverse transcriptase such as SuperScript IV (Life Technologies), in the presence of the corresponding buffer system. After RNA removal by RNase digestion such as RNase H, RNase If and/or RNase A (RNase from New England Biolabs and Thermo Scientific), second strand synthesis is carried out by DNA polymerase such as Bst 2.0 DNA polymerase, KAPA DNA polymerase, Q5 DNA polymerase, etc (New England Biolabs or KAPA Biosystems). A specific primer is used to initiate second strand synthesis, which could be single stranded DNA or RNA. Double stranded DNA after second strand synthesis is then column purified (Zymo Research or QIAGEN). The purified double stranded DNA is the linearly amplified product of the genomic DNA from a single cell or from other sources. The DNA may then be subjected to various analysis methods for quality control, including DNA BioAnalyzer and quantitative PCR analysis. The DNA is then ready for sequencing library preparation. During library preparation, the sonication, fragmentation and/or size selection step could be optionally skipped.

Example VII

DNA Fragment Size Analysis

Figure 5:
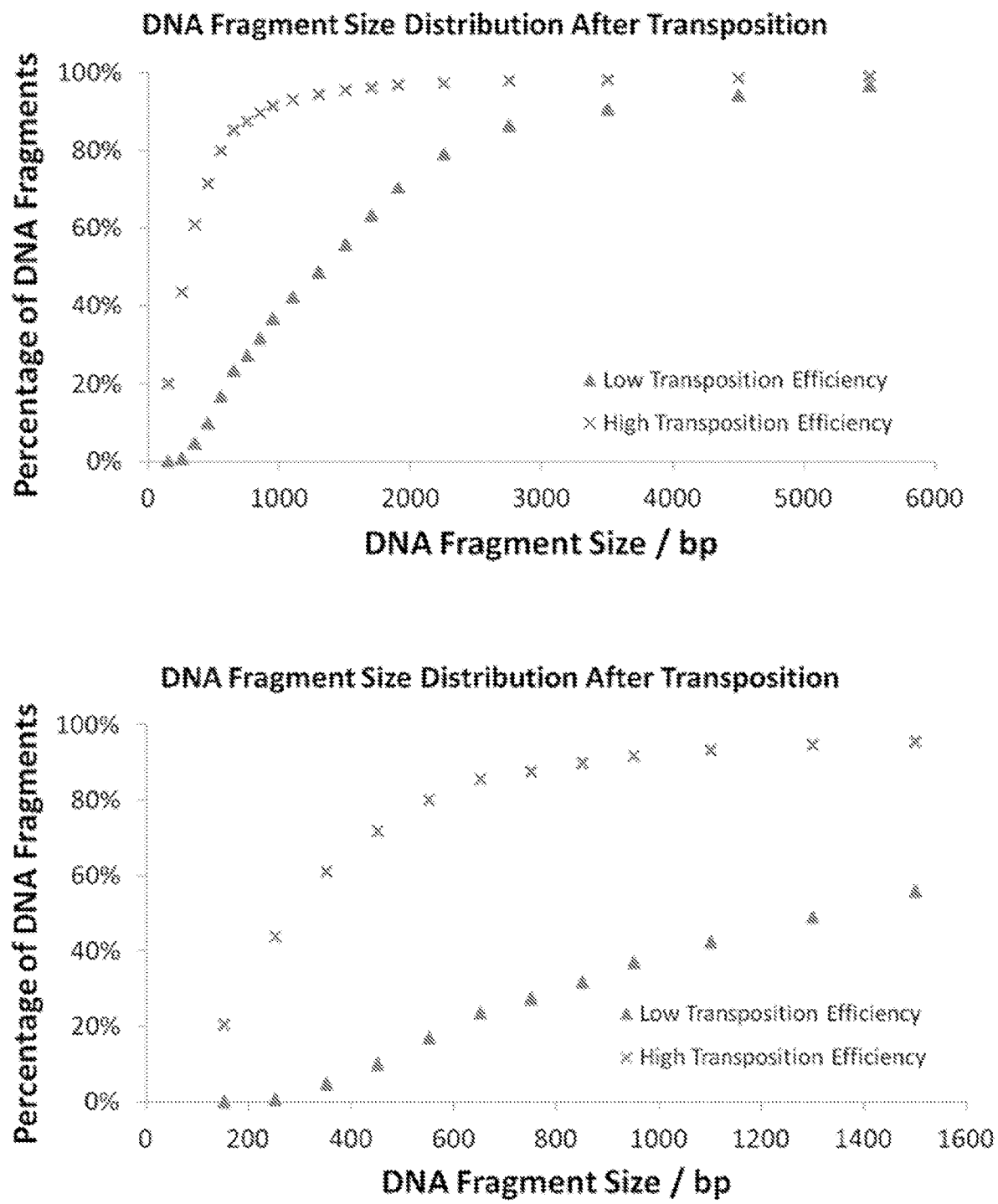
FIG. 5 depict graphs showing DNA fragment size distribution after transposition.

According to one aspect, the Tn5 transposome preparation and the transposition reaction conditions can be varied to result in different DNA fragment sizes. As shown in FIG. 5, the Tn5 transposition efficiency and the insertion density could be tuned at will within a large range. For the single-cell genome amplification, a post-transposition DNA fragment size of ~300 bp on average could be readily achieved. With reference to FIG. 5, the x-axis is the DNA fragment size, and the y-axis is the accumulated percentage of DNA fragments smaller than a given size. The bottom figure is a zoom-in on the x-axis of the top figure, showing finer details of the small-fragment-size region. The transposition efficiency and the insertion density could be tuned between the high efficiency and the low efficiency conditions. Under the condition for the high transposition efficiency, the average DNA fragment size is ~300 bp, with >90% of the DNA fragments <1 kb, which is a desirable distribution for IVT amplification and sequencing library preparation.

Example VIII

DNA Fragment Size Analysis

Figure 6:
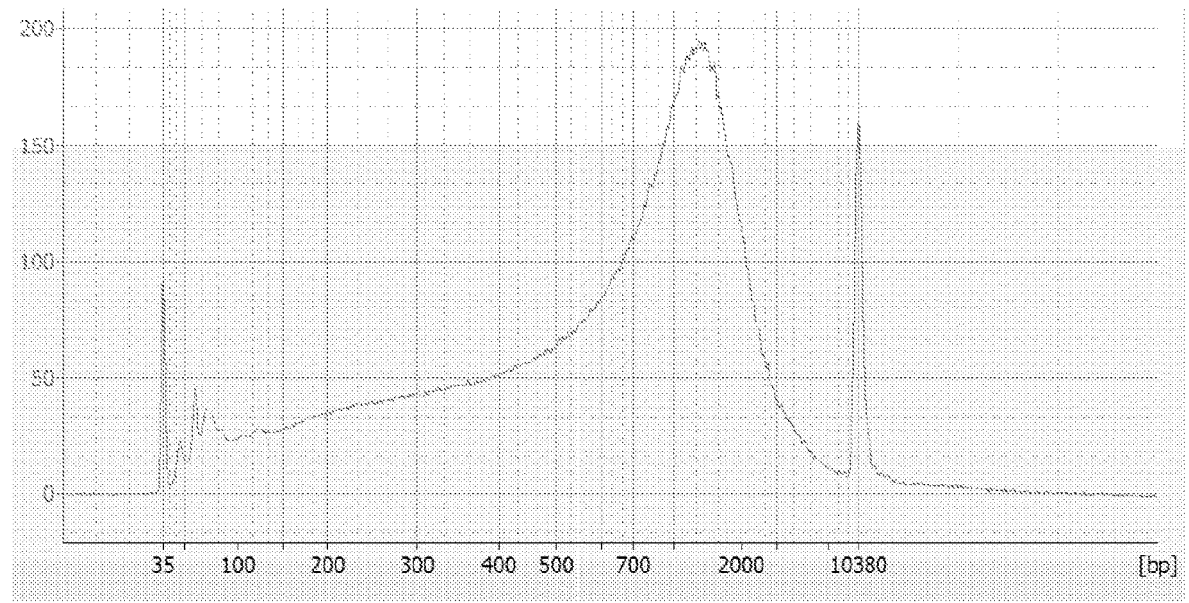
FIG. 6 is a graph showing DNA fragment size after amplification as determined by a DNA Bioanalyzer.

After single cell genomic DNA amplification as described herein, the product size distribution was probed by a DNA BioAnalyzer, the results of which are shown in FIG. 6. The x-axis is the fragment size, and the y-axis is the relative amount reflected by the fluorescence intensity with an arbitrary unit. The two sharp peaks at both sides of the image are the two spike-in DNA fragments of 35 bp and 10380 bp, respectively. The majority of the DNA fragments were several hundred by in size, suggesting an efficient transposition reaction on the single-cell gDNA templates, followed by the linear PVT amplification.

Figure 7:
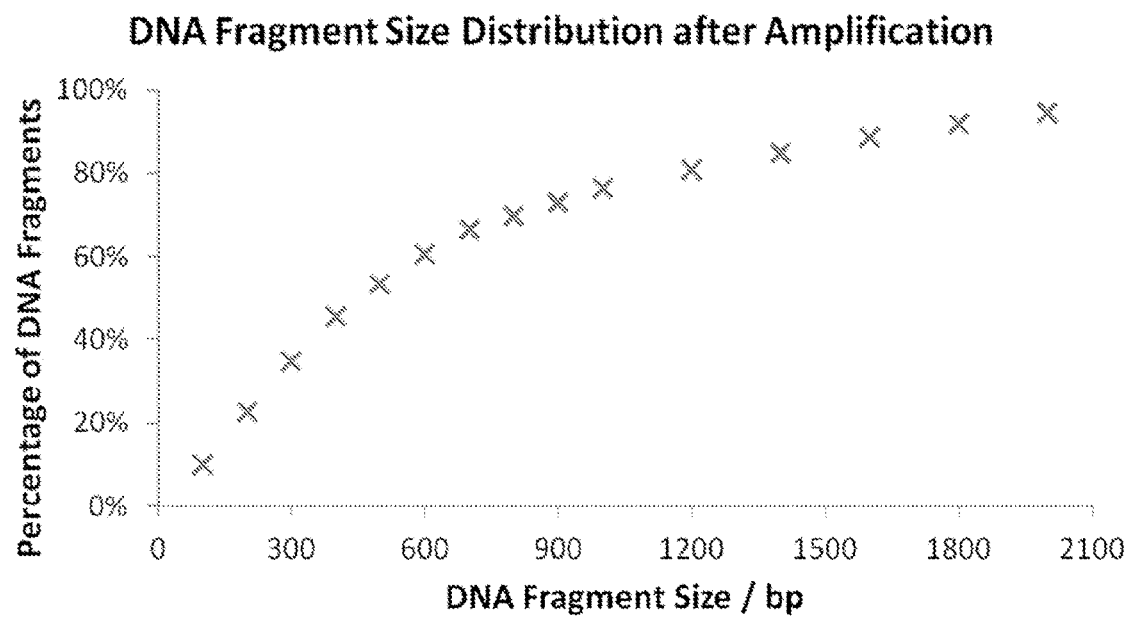
FIG. 7 is a graph showing DNA fragment size distribution after amplification.

To better interpret the fragment size distribution, an accumulative plot shown in FIG. 7 was drawn based on the DNA BioAnalyzer image. The x-axis is the DNA fragment size, and the y-axis is the accumulated percentage of the DNA fragments smaller than a given size. More than 80% of all the DNA fragments were shorter than 1.2 kb, and more than 95% of all the DNA fragments were shorter than 2 kb. Quantitative PCR results of 8 randomly picked genomic loci from the human genome showed a more or less equal representation of all the 8 loci compared with a bulk genomic DNA sample, suggesting a relatively even amplification using the methods described herein.

Example IX

Single Cell SNV Detection

Single nucleotide variations (SNV) in single cells may be analyzed using amplified DNA generated from the methods disclosed herein. When a particular SNV first emerges in a single cell, it is not detectable in a cell population by bulk sequencing. This highlights the need for single cell SNV calling. With exponential amplification, errors made in early amplification rounds get copied further in later rounds, and thus dominate the final pool of amplicons prior to sequencing as illustrated in FIG. 8. These amplification errors will overwhelm the true SNV signals in the original single-cell genomic DNA sample. With a PCR method shown at left of FIG. 8, an error "A=>T" in early rounds of amplification gets further amplified in later rounds, dominating the final bulk population and resulting in false positive in single-cell SNV calling.

With the methods of linear amplification described herein, every amplicon is copied directly from the original genomic DNA template, and an error occurs only once in a specific amplicon without further propagation. With an in vitro transcription method shown at right of FIG. 8, each amplicon is a direct copy from the original DNA template, and the errors made during amplification are located randomly in all positions. As a result, in the final bulk sample prior to sequencing, no amplification errors would dominate at a specific locus as illustrated in FIG. 8, and the true sequence of the original DNA template will be read out at a higher confidence level compared with that from exponential amplification, such as with PCR amplification, thereby enabling accurate single-cell SNV detection. By screening out the random errors and only focusing on the dominant base pairs in each locus, the original single-cell DNA template is faithfully amplified and sequenced, enabling single-cell SNV detection with a high confidence level.

Example X

Single Cell CNV Detection at a High Resolution

Copy number variations ("CNVs") are insertions, deletions or multiplications of genome segments, which can vary in size from kilobases to a whole chromosome. They are frequently observed in almost all categories of human tumors. Originating from a single cell, CNVs create genetic variations that are critical to the development and progression of tumors. The methods described herein allow the labeling of each genomic DNA fragment prior to amplification with a unique barcode designed in the transposon DNA as shown in FIG. 9. After amplification and sequencing of all the genomic DNA fragments, single-cell CNVs could be called and digitally counted at a resolution comparable with the transposition density (~1 kb), simply by counting the number of different barcodes associated to the same sequence pattern. This resolution for single-cell CNV detection is much higher than the current standard, which is 0.5-1 Mb fundamentally limited by the single-cell amplification noise.

Example XI

Single Cell SV Detection and De Novo Genome Assembly

Figure 10:
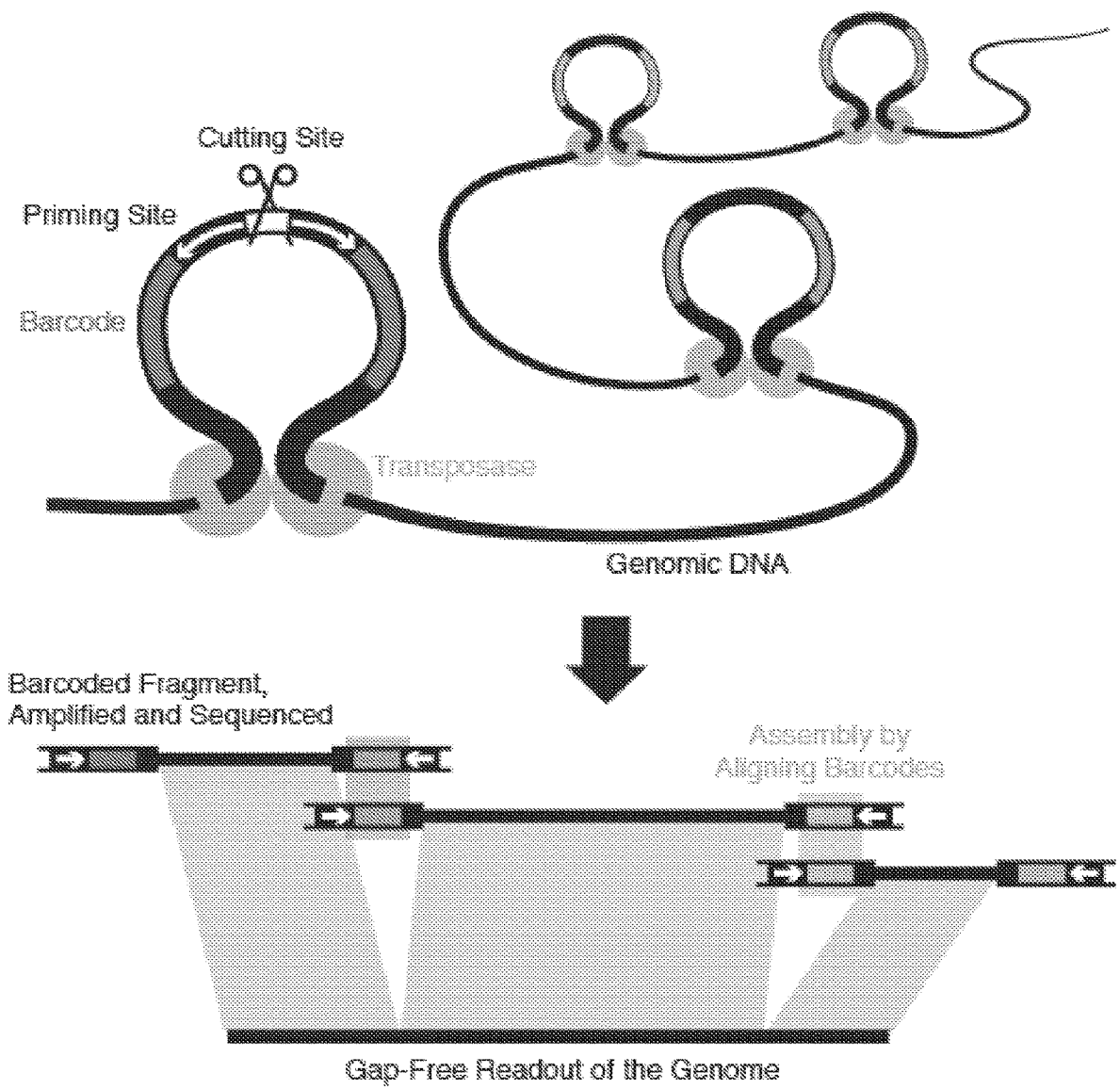
FIG. 10 is a schematic showing de novo genome assembly using a transposome with the transposon DNA including identical barcodes and priming sites separated by a cutting site. A plurality of transposomes bind to the genomic DNA and cuts the genomic DNA into fragments with each fragment having a different barcode on each end. The same barcodes can then be overlapped to assemble the DNA fragments into a genome without requiring a reference genome.

The methods described herein reduce or eliminate chimera formation during amplification allowing single cell structural variations ("SV") to be readily called. According to one aspect, transposome is prepared with two identical barcodes on both ends. This allows de novo assembly of a single-cell genome by matching the barcodes on both sides of each fragment, without the aid from the reference genome, as depicted in FIG. 10. After transposition, amplification and DNA sequencing, the fragments are readily assembled into each other by matching the barcodes on both ends of each fragment, enabling de novo assembly without the aid from the reference genome. This will not only enable de novo assembly of unknown genomes, but also greatly facilitate the mapping and assembly of the gaps full of the repetitive sequences in the current human reference genome.

Example XIII

Sequencing Results of Amplified Single-cell Genomic DNA

The methods described herein were performed to amplify the genomic DNA in a single cell picked from a normal human skin fibroblast cell line (BJ cell line). A single cell was picked by mouth pipetting into cell lysis buffer containing EDTA and QIAGEN Protease. The single cell lysis reaction was incubated at 55° C. for 3 hrs followed by 75° C. protease heat inactivation.

The single cell lysate was then mixed with Tn5 transposome in a buffer system containing 10 mM $Mg^{2+}$ and incubated at 55° C. for 15 min. dNTP mix and Bst 2.0 Warm Start DNA polymerase (New England Biolabs) was then added to fill the 9 bp gap on both ends of each fragment generated during transposition reaction and extend further downstream to form double stranded T7 promoters on both ends of each fragment. After the reaction, Bst 2.0 Warm Start DNA polymerase was heat inactivated at 80° C. for 20 minutes. The in vitro transcription assay was then assembled by adding essential components to the mixture, including T7 RNA polymerase (New England Biolabs), NTP mix, and T7 transcription buffer containing $Mg^{2+}$, DTT and Superase Inhibitor (Life Technologies). The T7 in vitro transcription assay was performed at 37° C. for 16 hours.

RNA was column purified (Zymo Research) acrd reverse transcribed by Superscript IV (Life Technologies). After RNA removal by RNase H and RNase If (New England Biolabs), second strand synthesis was carried out by KAPA DNA polymerase (KAPA Biosystems) using a specific single stranded DNA primer. The final double stranded DNA were linearly amplified products from the original genomic DNA in the single cell. DNA library with an average fragment size of 300 bp was made using NEBNext Ultra DNA library prep kit for Illumina (New England Biolabs), and pair-end sequenced by an Illumina HiSeq 2500 sequencer.

Figure 11:
FIG. 11 is the copy number variation (CNV) pattern of a single-cell genomic DNA after whole genome amplification and next generation sequencing. The single cell was picked from BJ cell line, a human skin fibroblast normal cell line. The bin size for each dot is 1 Mb. The flat. CNV pattern demonstrates the evenness of the single-cell genomic DNA amplification method.

The copy number variation (CNV) patterns of all 22 autosomes and the X chromosome were plotted as shown in FIG. 11 with a bin size of 1 Mb. The flat CNV pattern demonstrated a very good amplification evenness from the single-cell genomic DNA, enabling many single-cell applications relying on even amplification and accurate detection of CNV patterns across the genome.

The parameters of the sequencing run are summarized in FIG. 12. The sequencing data demonstrated high coverage given the sequencing depth, high accuracy as suggested by the low false positive rate, and low chimera rate. The high accuracy during single-cell genome amplification is a key requisite of single nucleotide variation (SNV) detection, and the low chimera rate is a key requisite of structural variation (SV) detection, both are very important to many applications based on single cell genomics.

Example XIII

Separation Techniques

Following amplification, it may be desirable to separate the amplification products of several different lengths from each other, from the template, and from excess primers for the purpose of analysis or more specifically for determining whether specific amplification has occurred.

In one embodiment, amplification products are separated by agarose, agarose-acrylamide or polyacrylamide gel electrophoresis using standard methods (Sambrook et al., "Molecular Cloning," A Laboratory Manual, 2d Ed., Cold Spring Harbor Laboratory Press, New York, 13.7-13.9: 1989). Gel electrophoresis techniques are well known in the art.

Alternatively, chromatographic techniques may be employed to effect separation. There are many kinds of chromatography which may be used in the present disclosure: adsorption, partition, ion-exchange, and molecular sieve, as well as many specialized techniques for using them including column, paper, thin-layer and gas chromatography (Freifelder, Physical Biochemstry Applications to Biochemistry and Molecular Biology, 2nd ed. Wm. Freeman and Co., New York, N.Y., 1982). Yet another alternative is to capture nucleic acid products labeled with, for example, biotin or antigen with beads bearing avidin or antibody, respectively.

Microfluidic techniques include separation on a platform such as microcapillaries, including by way of example those designed by ACLARA BioSciences Inc., or the LabChip™ by Caliper Technologies Inc. These microfluidic platforms require only nanoliter volumes of sample, in contrast to the microliter volumes required by other separation technologies. Miniaturizing some of the processes involved in genetic analysis has been achieved using microfluidic devices. For example, published PCT Application No. WO 94/05414, to Northrup and White, incorporated herein by reference, reports an integrated micro-PCR™ apparatus for collection and amplification of nucleic acids from a specimen. U.S. Pat. Nos. 5,304,487, 5,296,375, and 5,856,174 describe apparatus and methods incorporating the various processing and analytical operations involved in nucleic acid analysis and are incorporated herein by reference.

In some embodiments, it may be desirable to provide an additional, or alternative means for analyzing the amplified DNA. In these embodiments, microcapillary arrays are contemplated to be used for the analysis. Microcapillary array electrophoresis generally involves the use of a thin capillary or channel that may or may not be filled with a particular separation medium. Electrophoresis of a sample through the capillary provides a size based separation profile for the sample. Microcapillary array electrophoresis generally provides a rapid method for size-based sequencing, PCR™ product analysis, and restriction fragment sizing. The high surface to volume ratio of these capillaries allows for the application of higher electric fields across the capillary without substantial thermal variation across the capillary, consequently allowing for more rapid separations. Furthermore, when combined with confocal imaging methods, these methods provide sensitivity in the range of attomoles, which is comparable to the sensitivity of radioactive sequencing methods. Mierofabrication of microfluidic devices including microcapillary electrophoretic devices has been discussed in detail in, for example, Jacobson et al., Anal Chem, 66:1107-1113, 1994; Effenhauser et al., Anal Chem, 66:2949-2953, 1994; Harrison et al., Science, 261:895-897, 1993; Effenhauser et al., Anal Chem, 65:2637-2642, 1993; Manz et al., J. Chromatogr 593:253-258, 1992; and U.S. Pat. No. 5,904,824, incorporated herein by reference. Typically, these methods comprise photolithographic etching of micron scale channels on a silica, silicon, or other crystalline substrate or chip, and can be readily adapted for use in the present disclosure.

Tsuda et al. (Anal Chem, 62:2149-2152, 1990) describes rectangular capillaries, an alternative to the cylindrical capillary glass tubes. Some advantages of these systems are their efficient heat dissipation due to the large height-to-width ratio and, hence, their high surface-to-volume ratio and their high detection sensitivity for optical on-column detection modes. These flat separation channels have the ability to perform two-dimensional separations, with one force being applied across the separation channel, and with the sample zones detected by the use of a multi-channel array detector.

In many capillary electrophoresis methods, the capillaries, e.g., fused silica capillaries or channels etched, machined, or molded into planar substrates, are filled with an appropriate separation/sieving matrix. Typically, a variety of sieving matrices known in the art may be used in the microcapillary arrays. Examples of such matrices include, e.g., hydroxyethyl cellulose, polyacrylamide, agarose, and the like. Generally, the specific gel matrix, running buffers, and running conditions are selected to maximize the separation characteristics of the particular application, e.g., the size of the nucleic acid fragments, the required resolution, and the presence of native or undenatured nucleic acid molecules. For example, running buffers may include denaturants, chaotropic agents such as urea to denature nucleic acids in the sample.

Mass spectrometry provides a means of "weighing" individual molecules by ionizing the molecules in vacuo and making them "fly" by volatilization. Under the influence of combinations of electric and magnetic fields, the ions follow trajectories depending on their individual mass (m) and charge (z). For low molecular weight molecules, mass spectrometry has been part of the routine physical-organic repertoire for analysis and characterization of organic molecules by the determination of the mass of the parent molecular ion. In addition, by arranging collisions of this parent molecular ion with other particles (e.g., argon atoms), the molecular ion is fragmented forming secondary ions by the so-called collision induced dissociation (CID). The fragmentation pattern/pathway very often allows the derivation of detailed structural information. Other applications of mass spectrometric methods in the art are summarized in Methods in Enzymology, Vol. 193: "Mass Spectrometry" (J. A. McCloskey, editor), 1990, Academic Press, New York.

Due to the apparent analytical advantages of mass spectrometry in providing high detection sensitivity, accuracy of mass measurements, detailed structural information by CID in conjunction with an MS/MS configuration and speed, as well as on-line data transfer to a computer, there has been considerable interest in the use of mass spectrometry for the structural analysis of nucleic acids. Reviews summarizing this field include (Schram, Methods Biochem Anal, 34:203-287, 1990) and (Crain, Mass Spectrometry Reviews, 9:505-554, 1990), here incorporated herein by reference. The biggest hurdle to applying mass spectrometry to nucleic acids is the difficulty of volatilizing these very polar biopolymers. Therefore, "sequencing" had been limited to low molecular weight synthetic oligonucleotides by determining the mass of the parent molecular ion and through this, confirming the already known sequence, or alternatively, confirming the known sequence through the generation of secondary ions (fragment ions) via CID in an MS/MS configuration utilizing, in particular, for the ionization and volatilization, the method of fast atomic bombardment (FAB mass spectrometry) or plasma desorption (PD mass spectrometry). As an example, the application of FAB to the analysis of protected dimeric blocks for chemical synthesis of oligodeoxynucleotides has been described (Koster et al., Biomedical Environmental Mass Spectrometry 14:111-116, 1987).

Two ionization/desorption techniques are electrospray/ionspray (ES) and matrix-assisted laser desorption/ionization (MALDI). ES mass spectrometry was introduced by Fenn et al., J. Phys. Chem. 88; 4451-59, 1984; PCT Application No. WO 90/14148 and its applications are summarized in review articles, for example, Smith et al., Anal Chem 62:882-89, 1990, and Ardrey, Electrospray Mass Spectrometry, Spectroscopy Europe, 4:10-18, 1992. As a mass analyzer, a quadrupole is most frequently used. The determination of molecular weights in femtomole amounts of sample is very accurate due to the presence of multiple ion peaks that can be used for the mass calculation.

MALDI mass spectrometry, in contrast, can be particularly attractive when a time-of-flight (TOP) configuration is used as a mass analyzer. The MALDI-TOF mass spectrometry was introduced by (Hillenkamp et al., Biological Mass Spectrometry eds. Burlingame and McCloskey, Elsevier Science Publishers, Amsterdam, pp. 49-60, 1990). Since, in most cases, no multiple molecular ion peaks are produced with this technique, the mass spectra, in principle, look simpler compared to ES mass spectrometry. DNA molecules up to a molecular weight of 410,000 daltons could be desorbed and volatilized (Williams et al., Science, 246: 1585-87, 1989). More recently, the use of infrared lasers (FR) in this technique (as opposed to UV-lasers) has been shown to provide mass spectra of larger nucleic acids such as synthetic. DNA, restriction enzyme fragments of plasmid DNA, and RNA transcripts up to a size of 2180 nucleotides (Berkenkamp et al., Science, 281:260-2, 1998). Berkenkamp also describes how DNA and RNA samples can be analyzed by limited sample purification using MALDI-TOF IR.

In Japanese Patent No. 59-131909, an instrument is described that detects nucleic acid fragments separated either by electrophoresis, liquid chromatography or high speed gel filtration. Mass spectrometric detection is achieved by incorporating into the nucleic acids atoms that normally do not occur in DNA such as S, Br, I or Ag, Au, Pt, Os, Hg.

Labeling hybridization oligonucleotide probes with fluorescent labels is a well known technique in the art and is a sensitive, nonradioactive method for facilitating detection of probe hybridization. More recently developed detection methods employ the process of fluorescence energy transfer (PET) rather than direct detection of fluorescence intensity for detection of probe hybridization. PET occurs between a donor fluorophore and an acceptor dye (which may or may not be a fluorophore) when the absorption spectrum of one (the acceptor) overlaps the emission spectrum of the other (the donor) and the two dyes are in close proximity. Dyes with these properties are referred to as donor/acceptor dye pairs or energy transfer dye pairs. The excited-state energy of the donor fluorophore is transferred by a resonance dipole-induced dipole interaction to the neighboring acceptor. This results in quenching of donor fluorescence. In some cases, if the acceptor is also a fluorophore, the intensity of its fluorescence may be enhanced. The efficiency of energy transfer is highly dependent on the distance between the donor and acceptor, and equations predicting these relationships have been developed by Forster, Ann Phys 2:55-75, 1948. The distance between donor and acceptor dyes at which energy transfer efficiency is 50% is referred to as the Forster distance (Ro). Other mechanisms of fluorescence quenching are also known in the art including, for example, charge transfer and collisional quenching.

Energy transfer and other mechanisms that rely on the interaction of two dyes in close proximity to produce quenching are an attractive means for detecting or identifying nucleotide sequences, as such assays may be conducted in homogeneous formats. Homogeneous assay formats differ from conventional probe hybridization assays that rely on the detection of the fluorescence of a single fluorophore label because heterogeneous assays generally require additional steps to separate hybridized label from free label. Several formats for PET hybridization assays are reviewed in Nonisotopic DNA Probe Techniques (Academic Press, Inc., pgs. 311-352, 1992).

Homogeneous methods employing energy transfer or other mechanisms of fluorescence quenching for detection of nucleic acid amplification have also been described. Higuchi et al. (Biotechnology 10:413-417, 1992), discloses methods for detecting DNA amplification in real-time by monitoring increased fluorescence of ethidium bromide as it binds to double-stranded DNA. The sensitivity of this method is limited because binding of the ethidium bromide is not target specific and background amplification products are also detected. Lee et al. (Nucleic Acids Res 21:3761-3766, 1993), discloses areal-time detection method in which a doubly-labeled detector probe is cleaved in a target amplification-specific manner during PCR™. The detector probe is hybridized downstream of the amplification primer so that the 5'-3' exonuclease activity of Taq polymerase digests the detector probe, separating two fluorescent dyes, which then form an energy transfer pair. Fluorescence intensity increases as the probe is cleaved. Published PCT application WO 96/21144 discloses continuous fluorometric assays in which enzyme-mediated cleavage of nucleic acids results in increased fluorescence. Fluorescence energy transfer is suggested for use, but only in the context of a method employing a single fluorescent label that is quenched by hybridization to the target.

Signal primers or detector probes that hybridize to the target sequence downstream of the hybridization site of the amplification primers have been described for use in detection of nucleic acid amplification (U.S. Pat. No. 5,547,861). The signal primer is extended by the polymerase in a manner similar to extension of the amplification primers. Extension of the amplification primer displaces the extension product of the signal primer in a target amplification-dependent manner, producing a double-stranded secondary amplification product that may be detected as an indication of target amplification. The secondary amplification products generated from signal primers may be detected by means of a variety of labels and reporter groups, restriction sites in the signal primer that are cleaved to produce fragments of a characteristic size, capture groups, and structural features such as triple helices and recognition sites for double-stranded DNA binding proteins.

Many donor/acceptor dye pairs are known in the art and may be used in the present disclosure. These include but are not limited to: fluorescein isothiocyanate (FITC)/tetramethylrhodamine isothiocyanate (TALIC), FITC/Texas Red™ Molecular Probes, FITC/N-hydroxysuccmimidyl 1-pyrenebutyrate (PYB), FITC/eosin isothiocyanate (EITC), N-hydroxysuccinimidyl 1-pyrenesulfonate (PYS)/FITC, FITC/Rhodamine X, FITC/tetramethylrhodamine (TAMRA), and others. The selection of a particular donor/acceptor fluorophore pair is not critical. For energy transfer quenching mechanisms it is only necessary that the emission wavelengths of the donor fluorophore overlap the excitation wavelengths of the acceptor, i.e., there must be sufficient spectral overlap between the two dyes to allow efficient energy transfer, charge transfer, or fluorescence quenching. P-(dimethyl aminophenylazo) benzoic acid (DABCYL) is a non-fluorescent acceptor dye which effectively quenches fluorescence from an adjacent fluorophore, e.g., fluorescein or 5-(2'-aminoethyl) aminonaphthalene (EDANS). Any dye pairs that produce fluorescence quenching in the detector nucleic acids are suitable for use in the methods of the disclosure, regardless of the mechanism by which quenching occurs. Terminal and internal labeling methods are both known in the art and may be routinely used to link the donor and acceptor dyes at their respective sites in the detector nucleic acid.

Specifically contemplated in the present disclosure is the use or analysis of amplified products by microarrays and/or chip-based DNA technologies such as those described by (Hacia et al., Nature Genet, 14:441-449, 1996) and (Shoemaker et al., Nature Genetics, 14:450-456, 1996). These techniques involve quantitative methods for analyzing large numbers of genes rapidly and accurately. By tagging genes with oligonucleotides or using fixed probe arrays, chip technology can be employed to segregate target molecules as high density arrays and screen these molecules on the basis of hybridization (Pease et al., Proc Natl Acad Sci USA, 91:5022-5026, 1994; Fodor et al, Nature, 364:555-556, 1993).

Also contemplated is the use of BioStar's OIA technology to quantitate amplified products. OIA uses the mirror-like surface of a silicon wafer as a substrate. A thin film optical coating and capture antibody is attached to the silicon wafer. White light reflected through the coating appears as a golden background color. This color does not change until the thickness of the optical molecular thin film is changed.

When a positive sample is applied to the wafer, binding occurs between the ligand and the antibody. When substrate is added to complete the mass enhancement, a corresponding change in color from gold to purple/blue results from the increased thickness in the molecular thin film. The technique is described in U.S. Pat. No. 5,541,057, herein incorporated by reference.

Amplified RNA or DNA may be quantitated using the Real-Time PCR technique (Higuchi et al., Biotechnology 10:413-417, 1992). By determining the concentration of the amplified products that have completed the same number of cycles and are in their linear ranges, it is possible to determine the relative concentrations of the specific target sequence in the original DNA mixture. For example, if the DNA mixtures are cDNAs synthesized from RNAs isolated from different tissues or cells, the relative abundance of the specific mRNA from which the target sequence was derived can be determined for the respective tissues or cells. This direct proportionality between the concentration of the amplification products and the relative mRNA abundance is only true in the linear range of the amplification reaction.

The final concentration of the target DNA in the plateau portion of the curve is determined by the availability of reagents in the reaction mixture and is independent of the original concentration of target DNA. Therefore, the first condition that must be met before the relative abundance of a RNA or DNA species can be determined by Real-Time PCR for a collection of RNA or DNA populations is that the concentrations of the amplified products must be sampled when the reaction products are in the linear portion of their curves. The second condition that must be met for an RT-PCR experiment to successfully determine the relative abundance of a particular mRNA species is that relative concentrations of the amplifiable cDNAs must be normalized to some independent standard. The goal of a Real-Time PCR experiment is to determine the abundance of a particular RNA or DNA species relative to the average abundance of all RNA or DNA species in the sample.

The Luminex technology allows the quantitation of nucleic acid products immobilized on color coded microspheres. The magnitude of the biomolecular reaction is measured using a second molecule called a reporter. The reporter molecule signals the extent of the reaction by attaching to the molecules on the microspheres. As both the microspheres and the reporter molecules are color coded, digital signal processing allows the translation of signals into real-time, quantitative data for each reaction. The standard technique is described in U.S. Pat. Nos. 5,736,303 and 6,057,107, herein incorporated by reference.

Example XIV

Identification Techniques

Amplification products may be visualized in order to confirm amplification of the target-genets) sequences. One typical visualization method involves staining of a gel with a flourescent dye, such as ethidium bromide or Vistra Green, and visualization under UV light. Alternatively, if the amplification products are integrally labeled with radio- or fluorometrically-labeled nucleotides, the amplification products can be exposed to x-ray film or visualized under the appropriate stimulating spectra following separation.

In one embodiment, visualization is achieved indirectly, using a nucleic acid probe. Following separation of amplification products, a labeled, nucleic acid probe is brought into contact with the amplified products. The probe preferably is conjugated to a chromophore but may be radiolabeled. In another embodiment, the probe is conjugated to a binding partner, such as an antibody or biotin, where the other member of the binding pair carries a detectable moiety. In other embodiments, the probe incorporates a fluorescent dye or label. In yet other embodiments, the probe has a mass label that can be used to detect the molecule amplified. Other embodiments also contemplate the use of Taqman™ and Molecular Beacon™ probes. In still other embodiments, solid-phase capture methods combined with a standard probe may be used.

The type of label incorporated in DNA amplification products is dictated by the method used for analysis. When using capillary electrophoresis, microfluidic electrophoresis, HPLC, or LC separations, either incorporated or intercalated fluorescent dyes are used to label and detect the amplification products. Samples are detected dynamically, in that fluorescence is quantitated as a labeled species moves past the detector. If any electrophoretic method, HPLC, or LC is used for separation, products can be detected by absorption of UV light, a property inherent to DNA and therefore not requiring addition of a label. If polyacrylamide gel or slab gel electrophoresis is used, primers for the amplification reactions can be labeled with a fluorophore, a chromophore or a radioisotope, or by associated enzymatic reaction. Enzymatic detection involves binding an enzyme to a primer, e.g., via a biotin:avidin interaction, following separation of the amplification products on a gel, then detection by chemical reaction, such as chemiluminescence generated with luminal. A fluorescent signal can be monitored dynamically. Detection with a radioisotope or enzymatic reaction requires an initial separation by gel electrophoresis, followed by transfer of DNA molecules to a solid support (blot) prior to analysis. If blots are made, they can be analyzed more than once by probing, stripping the blot, and then reprobing. If amplification products are separated using a mass spectrometer no label is required because nucleic acids are detected directly.

A number of the above separation platforms can be coupled to achieve separations based on two different properties. For example, some of the PCR primers can be coupled with a moiety that allows affinity capture, while some primers remain unmodified. Modifications can include a sugar (for binding to a lectin column), a hydrophobic group (for binding to a reverse-phase column), biotin (for binding to a streptavidin column), or an antigen (for binding to an antibody column). Samples are run through an affinity chromatography column. The flow-through fraction is collected, and the bound fraction eluted (by chemical cleavage, salt elution, etc.). Each sample is then further fractionated based on a property, such as mass, to identify individual components.

Example XV

Kits

The materials and reagents required for the disclosed amplification method may be assembled together in a kit. The kits of the present disclosure generally will include at least the transposome (consists of transposase enzyme and transposon DNA), RNA polymerase, nucleotides, reverse transcriptase, and DNA polymerase necessary to carry out the claimed method along with primer sets as needed. In a preferred embodiment, the kit will also contain directions for amplifying DNA from DNA samples. Exemplary kits are those suitable for use in amplifying whole genomic DNA. In each case, the kits will preferably have distinct containers for each individual reagent, enzyme or reactant. Each agent will generally be suitably aliquoted in their respective containers. The container means of the kits will generally include at least one vial or test tube. Flasks, bottles, and other container means into which the reagents are placed and aliquoted are also possible. The individual containers of the kit will preferably be maintained in close confinement for commercial sale. Suitable larger containers may include injection or blow-molded plastic containers into which the desired vials are retained. Instructions are preferably provided with the kit.

Example XVI

Prenatal Diagnosis

According to certain aspects of the present disclosure, methods are provided for non-invasive prenatal diagnosis by amplifying genetic material, such as DNA, from a single fetal cell or group of fetal cells or circulating fetal DNA in maternal blood and then analyzing the genetic material. According to certain aspects the entire genome or significant portions of the genome of the fetus can be obtained and analyzed, for example, for fetal abnormalities, anomalies and disorders.

According to certain additional aspects, methods are provided for preimplantation genetic screening (PGS) and diagnosis (PGD). Over 100,000 in vitro fertilization (IVF) procedures are performed in the US every year, and techniques for screening embryos for implantation are desirable. Currently available PGS methods include biopsy procedures on polar body, blastomere, blastocyst, etc., followed by using genetic screening techniques such as fluorescence in situ hybridization (FISH) and polymerase chain reactions (PCR) for detecting specific chromosome aberrations (trisomy 21, etc.) and specific genetic variations known to cause severe phenotypical consequences. In IVF, embryos are grown to reach the two- to twelve-cell stage before implantation. According to certain aspects, a single cell or a few cells from the embryo are extracted and then the genetic material, such as DNA, is amplified according to the methods described herein whereby the entire genome of the embryo can be obtained and analyzed, for example, for fetal abnormalities, anomalies and disorders.

According to certain aspects, nucleated fetal cells from maternal blood are isolated. Nucleic acids, such as DNA, are extracted from a single nucleated fetal cell or from a plurality of nucleated fetal cells. Extracellular fetal nucleic acids can be obtained from maternal blood. See Lo et al., Nature Reviews Genetics, Vol. 8, pp. 71-77 (2007) and Lo et al., Sci. Transl. Med. 2, 61ra91 (2010) hereby incorporated by reference in their entireties. The nucleic acids are then amplified by the methods described herein using a transposase and an RNA polymerase to provide, for example, the entire genome of the fetus or specific genome loci for analysis. Genetic variations are then identified and associated with congenital disorders or with known phenotypical consequences.

Nucleated fetal cells are obtained as follows. Maternal blood is obtained by conventional venipuncture or finger pricking. About 0.1 ml to 100 ml of maternal blood is obtained. Nucleated fetal cells (including fetal nucleated red blood cells, lymphocytes, trophoblasts, etc.) can be isolated as early as ~8 weeks after gestation. Nucleated fetal cells from maternal circulation can be isolated by multiple different methods, including: fluorescence-activated cell sorting (FACS) by scattering and surface markers, magnetic-activated cell sorting, microdissection, cell size separation methods (e.g. by microfluidic devices), cell density separation methods (e.g. by centrifugation), etc.

Nucleic acids, such as DNA, is extracted from nucleated fetal cells as follows using protease assisted cell lysis. Single cells are lysed by 3 ul lysis buffer (30 mM Tris-Cl pH 7.8, 2 mM EDTA, 20 mM KCl, 0.3% Triton X-100, 30 mM dTT, 12.5 ug/ml Qiagen Protease). See, Bianchi et al., Isolation of fetal DNA from nucleated erythrocytes in maternal blood, Proc. Natl. Acad. Sci. USA Vol. 87, pp. 3279-3283, May 1990 and Wachtel et al., Clin. Genet. 2001: 59; 74-79 (2001) each hereby incorporated by reference in their entireties. Other methods such as alkaline lysis or freeze-thaw lysis can also be applied for nucleic acid extraction or using other methods described herein or known to those of skill in the art.

The single cell lysis was then mixed with Tn5 transposome in a buffer system containing 10 mM $Mg^{2+}$ and incubated at 55° C. for 15 min. After DNA fragmentation, dNTP mix and DNA polymerase such as Bst 2.0 Warm Start DNA polymerase (New England Biolabs) was added to fill the 9 bp gap left by transposition reaction and extend all the way down to both ends of each fragment to generate double stranded T7 promoter sequence. After the reaction, the Bst 2.0 Warm Start DNA polymerase could be optionally inactivated by 80° C. heating. The in vitro transcription assay was then assembled by adding essential components to the gap extension mixture, including T7 RNA polymerase (New England Biolabs), NTP mixture, and T7 transcription buffer containing $Mg^{2+}$ and DTT. Optionally RNase Inhibitors such as Superase (Life Technologies) could be added. The T7 in vitro transcription linear amplification reaction was performed up to 16 hrs at 37° C., in a volume between 30 □L to 100 □L, which could vary as necessary.

After the in vitro transcription, RNA was column purified (Zymo Research), reverse transcribed by reverse transcriptase such as Superscript IV (Life Technologies) in the presence of the corresponding buffer system. After RNA removal by RNase digestion such as RNase H and RNase If (New England Biolabs), second strand synthesis was carried out by DNA polymerase such as KAPA DNA polymerase (KAPA Biosystems). A specific single stranded DNA primer was used to initiate second strand synthesis followed by column purification (Zymo Research) of the resulting double stranded DNA. The purified double stranded DNA would be products linearly amplified from the minute amount of genomic DNA originally in the single cell.

The genetic analyses to be performed on the resulting amplified nucleic acids can be either on the scale of the whole genome, on selected but significant portions of the whole genome or on specific genome loci known to cause abnormalities. Examples of whole genome analyses includes whole genome sequencing by next generation sequencing methods (Illumina, SoliD, etc.), hybridization-based whole genome genotyping techniques such as Single Nucleotide Polymorphism (SNP) array, comparative genomic hybridization array, etc. Examples of analyzing significant portions of the whole genome includes targeted resequencing and genotyping on specific genome regions such as exome, specific chromosomes, etc. Examples of analyzing specific genome loci includes hybridizing nucleic acid probes to the resulting whole genome before imaging or sequencing the probes; as well as using PCR or multiplex PCR to amplify specific region(s) of the whole genome before further sequencing or genotyping these regions.

Genetic variations pertinent to prenatal screening and diagnosis mentioned above have a wide range of scale, including but not limited to single nucleotide variations (SNVs), small insertions and deletions (Indels) with size ranged 1-100 bp, copy number variations (CNVs) of genomic length ranged ~100 bp-100 Mbp, sequence inversions and duplications ranged 1 bp-10 Mbp, loss of heterozygosity (LOH) ranged 10 bp-100 Mbps, as well as whole chromosome level abnormalities such as chromosome translocations, aneuploidy, deletion or duplication of part or the whole chromosome.

Examples of "congenital disorders or known phenotypical consequences" include known disorders associated with the above-mentioned genetic variations, such as beta-thalassaemia caused by 4 bp deletion in codons 41 and 42 of the haemoglobin-beta (HBB) gene, and Down's syndrome caused by duplication of chromosome 21 (Trisomy 21). "Known phenotypical consequences" mentioned above include potential health conditions or physical status that are not recognized as congenital disorders, such as potential risks or disposition to certain diseases such as cancer, gender of the fetus, etc. For particular conditions see Cheung et al., Nature Genetics, Vol. 14, pp. 264-268 (1996) (sickle cell anemia and thalassaemia), Belroud, et al., The Lancet, Vol. 361, pp. 1013-1014 (2003) (spinal muscular atrophy)

According to certain additional aspects, one or more cells are biopsied or otherwise isolated from an IVF embryo. Nucleic acids, such as DNA, are extracted from a single cell or from a plurality of cells obtained from the IVF embryo. The nucleic acids are then amplified by the methods described herein using a transposase and an RNA polymerase to provide, for example, the entire genome of the embryo or specific genome loci for analysis. Genetic variations are then identified and associated with congenital disorders or with known phenotypical consequences.

One or more cells from an IVF embryo can be isolated by embryo puncture by micromanipulator. The biopsy or isolation is of a polar body from the embryo; is of trophectoderm from the embryo; is of blastomeres from the embryo, etc. The biopsy is taken from the embryo at day 0 to day 6 of development after fertilization.

Nucleic acids, such as DNA, is extracted from the embryonic cells as follows using protease assisted cell lysis. Single cells are lysed by 3 ul lysis buffer (30 mM Tris-Cl pH 7.8, 2 mM EDTA, 20 mM KCl, 0.3% Triton X-100, 30 mM dTT, 12.5 ug/ml Qiagen Protease). Other methods such as alkaline lysis or freeze-thaw lysis can also be applied for nucleic acid extraction or using other methods described herein or known to those of skill in the art.

The single cell lysis was then mixed with Tn5 transposome in a buffer system containing 10 mM $Mg^{2+}$ and incubated at 55° C. for 15 min. After DNA fragmentation, dNTP mix and DNA polymerase such as Bst 2.0 Warm Start DNA polymerase (New England Biolabs) was added to fill the 9 bp gap left by transposition reaction and extend all the way down to both ends of each fragment to generate double stranded T7 promoter sequence. After the reaction, the Bst 2.0 Warm Start DNA polymerase could be optionally inactivated by 80° C. heating. The in vitro transcription assay was then assembled by adding essential components to the gap extension mixture, including T7 RNA polymerase (New England Biolabs), NTP mixture, and T7 transcription buffer containing Mg$^{2+}$ and DTT. Optionally RNase Inhibitors such as Superase (Life Technologies) could be added. The T7 in vitro transcription linear amplification reaction was performed up to 16 hrs at 37° C., in a volume between 30 □L to 100 □L, which could vary as necessary.

After the in vitro transcription, RNA was column purified (Zymo Research), reverse transcribed by reverse transcriptase such as Superscript IV (Life Technologies) in the presence of the corresponding buffer system. After RNA removal by RNase digestion such as RNase H and RNase If (New England Biolabs), second strand synthesis was carried out by DNA polymerase such as KAPA DNA polymerase (KAPA Biosystems). A specific single stranded DNA primer was used to initiate second strand synthesis followed by column purification (Zymo Research) of the resulting double stranded DNA. The purified double stranded DNA would be products linearly amplified from the minute amount of genomic DNA originally in the single cell.

The genetic analyses to be performed on the resulting amplified nucleic acids can be either on the scale of the whole genome, on selected but significant portions of the whole genome or on specific genome loci known to cause abnormalities. Examples of whole genome analyses includes whole genome sequencing by next generation sequencing methods (Illumina, SoliD, etc.), hybridization-based whole genome genotyping techniques such as Single Nucleotide Polymorphism (SNP) array, comparative genomic hybridization array, etc. Examples of analyzing significant portions of the whole genome includes targeted resequencing and genotyping on specific genome regions such as exome, specific chromosomes, etc. Examples of analyzing specific genome loci includes hybridizing nucleic acid probes to the resulting whole genome before imaging or sequencing the probes; as well as using PCR or multiplex PCR to amplify specific region(s) of the whole genome before further sequencing or genotyping these regions.

Genetic variations pertinent to prenatal screening and diagnosis mentioned above have a wide range of scale, including but not limited to single nucleotide variations (SNVs), small insertions and deletions (Indels) with size ranged 1-100 bp, copy number variations (CNVs) of genomic length ranged ~100 bp-100 Mbp, sequence inversions and duplications ranged 1 bp-10 Mbp, loss of heterozygosity (LOH) ranged 10 bp-100 Mbps, as well as whole chromosome level abnormalities such as chromosome translocations, aneuploidy, deletion or duplication of part or the whole chromosome and other chromosomal disorders and genetic disorders known to those of skill in the art. It is to be understood that the listing of certain disorders herein is not intended to be exhaustive but only exemplary. As the methods described herein are intended to analyze the genome of a single cell, any and all disorders that can be identified by analyzing the genome of a cell are included herein as being exemplary of the present disclosure.

Examples of "congenital disorders or known phenotypical consequences" subject to prenatal diagnosis include known disorders associated with the above-mentioned genetic variations, such as beta-thalassaemia caused by 4 bp deletion in codons 41 and 42 of the haemoglobin-beta (HBB) gene, and chromosomal disorders such as Down's syndrome caused by duplication of chromosome 21 (Trisomy 21). "Known phenotypical consequences" mentioned above include potential health conditions or physical status that are not recognized as congenital disorders, such as potential risks or disposition to certain diseases such as cancer, gender of the fetus, etc. Additional disorders which can be diagnosed for a fetus (prenatal diagnosis) or embryo using the methods described herein include cystic fibrosis, sickle cell disease, tay-sachs disease, fragile X syndrome, spinal muscular atrophy, haemoglobinopathies, alpha-thalassemia, X-linked disorders (disorders determined by genes on the X chromosome), spina bifida, anencephaly, congenital heart defects, obesity, diabetes, cancer, fetal gender, fetal RHD, fetal HLA haplotype, paternally derived mutations, chromosomal aneuploidy, etc.

Example XVII

Cancer Diagnosis

According to certain aspects of the present disclosure, methods are provided for performing whole genome genetic analysis on a single cancer cell, a few cancer cells, a plurality of cancer cells or a minimal amount of cancer cell material. The present methods are particularly useful where only small amounts of cancer cells are present, i.e. a rare amount, or are able to be obtained or isolated. Examples of such cancer cells include circulating tumor cells (CTCs) in the blood of an individual. During the process of interaction of tumor cells with blood vessels, as well as, metastasis, cancer cells such as tumor cells will invade into the bloodstream. Current diagnostic methods using circulating tumor cells rely on counting of enriched CTC cells. Due to the rare amount of CTC cells in the blood (as rare as 1 in 109 blood cells) and the heterogeneity of CTCs, the enrichment efficiency varies case by case. Counting of CTCs is less reliable and the method is currently under evaluation in clinical trials. CellSearch is the only FDA approved machine for CTC enrichment and counting. The conventional genetic diagnosis with the requirement of ~1 million cells may not be applied to CTCs.

Circulating tumor cells provide a course of cells derived from primary or metastatic sites allowing detection and analysis of cancer cells providing an early diagnosis. Methods described herein allow analysis of DNA from circulating tumor cells, which are usually few or rare in number, as a method of diagnosing an individual with cancer without invasive techniques such as obtaining a sample of tumor tissue by surgical means. Methods described herein allow analysis of DNA from circulating tumor cells, which are usually few or rare in number, as a method of early diagnosis of cancer in an individual where the cancer may be at a very early stage, but nonetheless at a point where cancer cells enter the bloodstream of the individual. Methods described herein provide reliable whole genome amplification that can uniformly amplify the whole genome of single cells, as well as about 10 to about 100 cells, without introducing significant amplification bias and allelic drop-outs. Since the methods described herein can amplify the whole genome or near whole genome of a single cell, the methods described herein have particular utility with circulating tumor cells which are relatively few in number, but can still provide an important early detection of cancer.

According to one aspect, the methods described herein using a transposase and an RNA polymerase are capable of whole genome amplification of a single cancer cell, such as a tumor cell such as a circulating tumor cell for further analysis. According to one aspect, circulating tumor cells can be enriched from a patient's bloodstream. Tumor cells can also be obtained from a primary site or metastasis by non-open surgery such as fine-needle aspiration (FNA) to provide a sample for minimum sample mass diagnosis (MSMD). In this manner, the obtaining of one or more tumor cells can be considered non-invasive. While the methods described herein have particular application to situations where only a rare amount of cancer cells are available, one of skill in the art will readily understand that the methods also have application where a large amount of cancer cells are available, but where single cell genetic analysis is desired.

According to one aspect, methods for analyzing DNA from a cancer cell are provided. The term "cancer" refers to various types of malignant neoplasms, most of which can invade surrounding tissues, and may metastasize to different sites (see, for example, PDR Medical Dictionary 1st edition (1995)). The terms "neoplasm" and "tumor" refer to an abnormal tissue that grows by cellular proliferation more rapidly than normal and continues to grow after the stimuli that initiated proliferation is removed. Id. Such abnormal tissue shows partial or complete lack of structural organization and functional coordination with the normal tissue which may be either benign (i.e., benign tumor) or malignant (i.e., malignant tumor).

Examples of general categories of cancer include, but are not limited to, carcinomas malignant tumors derived from epithelial cells such as, for example, common forms of breast, prostate, lung and colon cancer), sarcomas (i.e., malignant tumors derived from connective tissue or mesenchymal cells), lymphomas (i.e., malignancies derived from hematopoietic cells), leukemias (i.e., malignancies derived from hematopoietic cells), germ cell tumors (i.e., tumors derived from totipotent cells; in adults most often found in the testicle or ovary; in fetuses, babies and young children, most often found on the body midline, particularly at the tip of the tailbone), blastic tumors (i.e., a typically malignant tumor which resembles an immature or embryonic tissue) and the like. One of skill in the art will understand that this list is exemplary only and is not exhaustive, as one of skill in the art will readily be able to identify additional cancers based on the disclosure herein.

Examples of specific neoplasms intended to be encompassed by the present invention include, but are not limited to, acute lymphoblastic leukemia; myeloid leukemia, acute myeloid leukemia, childhood; adrenocortical carcinoma; AIDS-related cancers; AIDS-related lymphoma; anal cancer; appendix cancer; astrocytoma (e.g., cerebellar, cerebral); atypical teratoid/rhabdoid tumor; basal cell carcinoma; bile duct cancer, extrahepatic; bladder cancer; bone cancer, osteosarcoma and malignant fibrous histiocytoma; brain tumor (e.g., brain stem glioma, central nervous system atypical teratoid/rhabdoid tumors, central nervous system embryonal tumors, cerebellar astrocytoma, cerebral astrocytoma/malignant glioma, craniopharyngioma, ependymoblastoma, ependymoma, medulloblastoma, medulloepithelioma, pineal parenchymal tumors of intermediate differentiation, supratentorial primitive neuroectodermal tumors and/or pineoblastoma, visual pathway and/or hypothalamic glioma, brain and spinal cord tumors); breast cancer; bronchial tumors; Burkitt lymphoma; carcinoid tumor (e.g., gastrointestinal); carcinoma of unknown primary; central nervous system (e.g., atypical teratoid/rhabdoid tumor, embryonal tumors (e.g., lymphoma, primary); cerebellar astrocytoma; cerebral astrocytoma/malignant glioma; cervical cancer; chordoma; chronic lymphocytic leukemia; chronic myelogenous leukemia; chronic myeloproliferative disorders; colon cancer; colorectal cancer; craniopharyngioma; cutaneous T-cell lymphoma; embryonal tumors, central nervous system; endometrial cancer; ependymoblastoma; ependymoma; esophageal cancer; Ewing family of tumors; extracranial germ cell tumor; extragonadal germ cell tumor; extrahepatic bile duct cancer; eye cancer (e.g., intraocular melanoma, retinoblastoma); gallbladder cancer; gastric cancer; gastrointestinal tumor (e.g., carcinoid tumor, stromal tumor (gist), stromal cell tumor); germ cell tumor (e.g., extracranial, extragonadal, ovarian); gestational trophoblastic tumor; glioma (e.g., brain stem, cerebral astrocytoma); hairy cell leukemia; head and neck cancer; hepatocellular cancer; Hodgkin lymphoma; hypopharyngeal cancer; hypothalamic and visual pathway glioma; intraocular melanoma; islet cell tumors; Kaposi sarcoma; kidney cancer; large cell tumors; laryngeal cancer (e.g., acute lymphoblastic, acute myeloid); leukemia (e.g., acute myeloid, chronic lymphocytic, chronic myelogenous, hairy cell); lip and/or oral cavity cancer; liver cancer; lung cancer (e.g., non-small cell, small cell); lymphoma (e.g., AIDS-related, Burkitt, cutaneous Tcell, Hodgkin, non-Hodgkin, primary central nervous system); macroglobulinemia, Waldenström; malignant fibrous histiocytoma of bone and/or osteosarcoma; medulloblastoma; medulloepithelioma; melanoma; merkel cell carcinoma; mesothelioma; metastatic squamous neck cancer; mouth cancer; multiple endocrine neoplasia syndrome; multiple myeloma/plasma cell neoplasm; mycosis fungoides; myelodysplastic syndromes; myelodysplastic/myeloproliferative diseases; myelogenous leukemia (e.g., chronic, acute, multiple); myeloproliferative disorders, chronic; nasal cavity and/or paranasal sinus cancer; nasopharyngeal cancer; neuroblastoma; non-Hodgkin lymphoma; non-small cell lung cancer; oral cancer; oral cavity cancer, oropharyngeal cancer; osteosarcoma and/or malignant fibrous histiocytoma of bone; ovarian cancer (e.g., ovarian epithelial cancer, ovarian germ cell tumor, ovarian low malignant potential tumor); pancreatic cancer (e.g., islet cell tumors); papillomatosis; paranasal sinus and/or nasal cavity cancer; parathyroid cancer; penile cancer; pharyngeal cancer; pheochromocytoma; pineal parenchymal tumors of intermediate differentiation; pineoblastoma and supratentorial primitive neuroectodermal tumors; pituitary tumor; plasma cell neoplasm/multiple myeloma; pleuropulmonary blastoma; primary central nervous system lymphoma; prostate cancer; rectal cancer; renal cell cancer; renal, pelvis and/or ureter, transitional cell cancer; respiratory tract carcinoma involving the nut gene on chromosome 15; retinoblastoma; rhabdomyosarcoma; salivary gland cancer; sarcoma (e.g., Ewing family of tumors, Kaposi, soft tissue, uterine); Sézary syndrome; skin cancer (e.g., non-melanoma, melanoma, merkel cell); small cell lung cancer; small intestine cancer; soft tissue sarcoma; squamous cell carcinoma; squamous neck cancer with occult primary, metastatic; stomach cancer; supratentorial primitive neuroectodermal tumors; T-cell lymphoma, cutaneous; testicular cancer; throat cancer; thymoma and/or thymic carcinoma; thyroid cancer; transitional cell cancer of the renal, pelvis and/or ureter; trophoblastic tumor; unknown primary site carcinoma; urethral cancer; uterine cancer, endometrial; uterine sarcoma; vaginal cancer; visual pathway and/or hypothalamic glioma; vulvar cancer; Waldenstrom macroglobulinemia; Wilms tumor and the like. For a review, see the National Cancer Institute's Worldwide Website (cancer.gov/cancertopics/alphalist). One of skill in the art will understand that this list is exemplary only and is not exhaustive, as one of skill in the art will readily be able to identify additional cancers and/or neoplasms based on the disclosure herein.

According to certain aspects, circulating tumor cells from the blood of an individual are isolated. Nucleic acids are extracted from one or more circulating tumor cells. The nucleic acids are then amplified by the amplification methods described herein, to provide, for example, the entire genome of the cell or specific genome loci for analysis. The genome is then analyzed for genetic variations that are associate with genomic disorders in cancer.

Circulating tumor cells are obtained as follows. Patient blood is obtained by conventional venipuncture. About 10 ml of blood is obtained. Circulating tumor cells can be isolated by multiple different methods, including: commercial CellSearch system (see Clin. Cancer Res. 2004, 10, 6897-6904 and Clin. Cancer Res. 2010, 16, 2634-2645 each hereby incorporated by reference in its entirety), size based filtration device (see Am. J. Pathol. 2000, 156, 57-63 and Cancer Res. 2010, 70, 6420-6428 each hereby incorporated by reference in its entirety), wild-field imaging with fiber-optic array scanning technology (see Proc. Natl. Acad. Sci. USA 2004, 101, 10501-10504 hereby incorporated by reference in its entirety), antibody-based surface capture in tailored microfluidic devices (see Lab Chip 2010, 10, 837-842, Nature 2007, 450, 1235-1239, Anal. Chem. 2011, 83, 2301-2309, Angew. Chem. 2011, 123, 3140-3144 and Angew. Chem. Int. Ed. 2011, 50, 3084-3088 each hereby incorporated by reference in its entirety.)

According to certain additional aspects, one or more cells are obtained by fine needle aspiration to isolate cells from a lump or a tissue mass. Nucleic acids, such as DNA, are extracted from a single cell or from a plurality of cells obtained from the fine needle aspiration. The nucleic acids are then amplified by the methods described herein using a transposase and an RNA polymerase to provide, for example, the entire genome of the embryo or specific genome loci for analysis. Genetic variations are then identified and associated with congenital disorders or with known phenotypical consequences.

Cells are biopsied and isolated using fine needle aspiration as follows. The skin above the area to be biopsied is swabbed with an antiseptic solution and draped with sterile surgical towels. After locating the mass for biopsy, using x-rays or palpation, a special needle of very fine diameter (22 or 25 gauge) is passed into the mass. After the needles are placed into the mass, cells are withdrawn by aspiration with a syringe and transferred to a single tube. Cells are preserved and labeled by markers. Single cancer cells are isolated under fluorescent microscope with mouth pipetting or laser dissection.

Nucleic acids, such as DNA, are extracted from CTC cells or cells obtained by fine needle aspiration as follows using protease assisted cell lysis. Single cells are lysed by 3 ul lysis buffer (30 mM Tris-Cl pH 7.8, 2 mM EDTA, 20 mM KCl, 0.3% Triton X-100, 30 mM dTT, 12.5 ug/ml Qiagen Protease). Other methods such as alkaline lysis or freeze-thaw lysis can also be applied for nucleic acid extraction or using other methods described herein or known to those of skill in the art.

The single cell lysis was then mixed with Tn5 transposome in a buffer system containing 10 mM $Mg^{2+}$ and incubated at 55° C. for 15 min. After DNA fragmentation, dNTP mix and DNA polymerase such as Bst 2.0 Warm Start DNA polymerase (New England Biolabs) was added to fill the 9 bp gap left by transposition reaction and extend all the way down to both ends of each fragment to generate double stranded T7 promoter sequence. After the reaction, the Bst 2.0 Warm Start DNA polymerase could be optionally inactivated by 80° C. heating. The in vitro transcription assay was then assembled by adding essential components to the gap extension mixture, including T7 RNA polymerase (New England Biolabs), NTP mixture, and T7 transcription buffer containing $Mg^{2+}$ and DTT. Optionally RNase Inhibitors such as Superase (Life Technologies) could be added. The T7 in vitro transcription linear amplification reaction was performed up to 16 hrs at 37° C., in a volume between 30 □L to 100 □L, which could vary as necessary.

After the in vitro transcription, RNA was column purified (Zymo Research), reverse transcribed by reverse transcriptase such as Superscript IV (Life Technologies) in the presence of the corresponding buffer system. After RNA removal by RNase digestion such as RNase H and RNase If (New England Biolabs), second strand synthesis was carried out by DNA polymerase such as KAPA DNA polymerase (KAPA Biosystems). A specific single stranded DNA primer was used to initiate second strand synthesis followed by column purification (Zymo Research) of the resulting double stranded DNA. The purified double stranded DNA would be products linearly amplified from the minute amount of genomic DNA originally in the single cell.

The genetic analyses to be performed on the resulting amplified nucleic acids can be either on the scale of the whole genome, on selected but significant portions of the whole genome or on specific genome loci known to cause abnormalities. Examples of whole genome analyses includes whole genome sequencing by next generation sequencing methods (Illumines, SoliD, etc.), hybridization-based whole genome genotyping techniques such as Single Nucleotide Polymorphism (SNP) array, comparative genomic hybridization array, etc. Examples of analyzing significant portions of the whole genome includes targeted resequencing and genotyping on specific genome regions such as exome, specific chromosomes, etc. Examples of analyzing specific genome loci includes hybridizing nucleic acid probes to the resulting whole genome amplification product before imaging or sequencing the probes; as well as using PCR or multiplex PCR to amplify specific region(s) of the whole genome before further sequencing or genotyping these regions.

Genetic variations pertinent to cancer diagnosis mentioned above have a wide range of scale, including but not limited to single nucleotide variations (SNVs), small insertions and deletions (Indels) with size ranging 1-100 bp, copy number variations (CNVs) of genomic length ranging ~100 bp-100 Mbp, sequence inversions and duplications ranging 1 bp-10 Mbp, loss of heterozygosity (LOH) ranging 10 bp-100 Mbps, as well as whole chromosome level abnormalities such as chromosome translocations, aneuploidy, deletion or duplication of part or the whole chromosome.

Examples of existing cancer genome variations are provided in publicly available databases including Cancer Genome Anatomy Project (CGA) from NIH and Catalogue of Somatic Mutations in Cancer (COSMIC).

What is claimed is:

1. A method of single cell whole genome amplification and sequencing comprising contacting double stranded genomic DNA from a single cell with Tn5 transposases each complexed with a transposon DNA, wherein the transposon DNA includes a double-stranded 19 bp Tnp binding site and an overhang, wherein the overhang includes a barcode region, a priming site and a strong T7 promoter sequence, wherein the Tn5 transposase/transposon DNA complex bind to target locations along the double stranded genomic DNA cleaving the double stranded genomic DNA into a plurality of double stranded fragments, with each double stranded fragment having a first complex attached to an upper strand by the Tnp binding site and a second complex attached to a lower strand by the Tnp binding site, removing the Tn5 transposases from the complex, extending the double stranded fragments along the transposon DNA to make a double stranded extension product having T7 promoters at each end, contacting the double stranded extension product with T7 RNA polymerase to make RNA transcripts of the double stranded extension product, reverse transcribing the RNA transcript into single stranded DNA, and forming a complementary strand to the single stranded DNA to form a double stranded DNA including the genomic DNA sequence and having barcodes at both ends of the upper and lower strands.

2. A method of nucleic acid amplification comprising contacting a double stranded nucleic acid with transposases bound to transposon DNA, wherein the transposon DNA includes a transposase binding site, wherein the transposase/transposon DNA complex bind to target locations along the double stranded nucleic acid and cleave the double stranded nucleic acid into a plurality of double stranded fragments, with each double stranded fragment having the transposon DNA bound to each 5' end of the double stranded fragment, extending the double stranded fragments along the transposon DNA to make double stranded extension products at each end, and amplifying the double stranded extension products.

3. The method of claim 2 wherein the double stranded nucleic acid is an isolated double stranded nucleic acid and the transposase is an isolated transposase.

4. The method of claim 2 wherein the double stranded nucleic acid is genomic DNA.

5. The method of claim 2 wherein the double stranded nucleic acid is genomic DNA obtained from a single cell.

6. The method of claim 2 wherein the double stranded nucleic acid is the whole genome of a single cell.

7. The method of claim 2 wherein the transposase is Tn5 transposase.

8. The method of claim 2 wherein the transposon DNA further includes a barcode sequence and/or a priming site.

9. The method of claim 2 wherein the transposon DNA includes a double-stranded 19 bp Tnp binding site and an overhang, wherein the overhang includes a barcode region and a priming site.

10. The method of claim 2 wherein the transposon DNA includes a double-stranded 19 bp Tnp binding site and a nucleic acid loop structure including a barcode region and a priming site.

11. The method of claim 2 wherein bound transposases are removed from the double stranded fragments before extending the double stranded fragments.

12. The method of claim 2 wherein the transposases are Tn5 transposases each complexed with a transposon DNA, wherein the transposon DNA includes a double-stranded 19 bp Tnp binding site and an overhang, wherein the overhang includes a barcode region and a priming site, wherein the Tn5 transposase/transposon DNA complex bind to target locations along the double stranded genomic DNA cleaving the double stranded genomic DNA into a plurality of double stranded fragments.

13. The method of claim 2 further including the step of sequencing the double stranded extension products.

14. The method of claim 2 further including the step of detecting single nucleotide variations, detecting copy number variations, or detecting structural variations in the double stranded extension products.

15. The method of claim 2 wherein the double stranded nucleic acid is genomic DNA from a prenatal cell, a cancer cell, or a circulating tumor cell.

16. The method of claim 2 wherein the double stranded nucleic acid is genomic DNA from a single prenatal cell, a single cancer cell, or a single circulating tumor cell.

17. The method of claim 2 wherein the transposon DNA further comprises an RNA polymerase promoter sequence and wherein the double stranded extension products comprise double stranded RNA polymerase promoter sequences at each end.

18. The method of claim 17 wherein the RNA polymerase promoter sequence is a T7 promoter sequence.

19. The method of claim 17 further comprising contacting the double stranded extension products with an RNA polymerase to make a plurality of RNA transcripts of each double stranded extension product, reverse transcribing the RNA transcripts into single stranded copy DNA, and forming complementary strands to the single stranded copy DNA to form a plurality of double stranded DNA amplicons corresponding to each double stranded fragment, wherein the double stranded DNA amplicons are linearly amplified from the original double stranded fragments.

20. The method of claim 19 wherein the RNA polymerase is T7 RNA polymerase.

* * * * *